United States Patent
De Kort et al.

(10) Patent No.: US 10,264,806 B2
(45) Date of Patent: Apr. 23, 2019

(54) CONTROLLING THE TEXTURE OF HIGH-PROTEIN NUTRITIONAL COMPOSITIONS COMPRISING MICELLAR CASEIN

(75) Inventors: Esther Jacqueline De Kort, Wageningen (NL); Marcel Minor, Wageningen (NL)

(73) Assignee: N.V. NUTRICIA, Zoetermeer (NL)

( * ) Notice: Subject to any disclaimer, the term of this patent is extended or adjusted under 35 U.S.C. 154(b) by 622 days.

(21) Appl. No.: 13/583,896

(22) PCT Filed: Mar. 11, 2011

(86) PCT No.: PCT/NL2011/050168
§ 371 (c)(1),
(2), (4) Date: Nov. 19, 2012

(87) PCT Pub. No.: WO2011/112087
PCT Pub. Date: Sep. 15, 2011

(65) Prior Publication Data
US 2013/0065824 A1    Mar. 14, 2013

(30) Foreign Application Priority Data
Mar. 11, 2010    (WO) ................ PCT/NL2010/050129

(51) Int. Cl.
| | | |
|---|---|---|
| A23J 3/10 | (2006.01) | |
| A23L 29/00 | (2016.01) | |
| A23L 33/00 | (2016.01) | |
| A23L 33/19 | (2016.01) | |

(52) U.S. Cl.
CPC .............. *A23J 3/10* (2013.01); *A23L 29/015* (2016.08); *A23L 29/035* (2016.08); *A23L 33/19* (2016.08); *A23L 33/40* (2016.08); *A23V 2002/00* (2013.01)

(58) Field of Classification Search
None
See application file for complete search history.

(56) References Cited

U.S. PATENT DOCUMENTS 5,683,984 A    11/1997 Jost
6,455,082 B1   9/2002 Sher et al.

FOREIGN PATENT DOCUMENTS

| WO | WO-01/72135 A1 | 10/2001 | |
| WO | WO 2009/072885 | * | 6/2009 |
| WO | WO-2009/072885 A1 | 6/2009 | |

OTHER PUBLICATIONS

Wang et al, Dietary Uridine-5'-Monophosphate Supplementation Increases Potassium-Evoked Dopamine Release and Promotes Neurite Outgrowth in Aged Rats, J Mol Neurosci, 2005;27(1):137-45.*
Miyazaki et al, Effects of Nucleotides on Learning and Memory in a Morris Water Maze Test in Normal and Basal Forebrain-Lesioned Rats, (Life Sciences, vol. 64. No. 1, pp. 45-52, 1999).*
CMP hmdb00095, downloaede online from URL:<http://www.hmdb.ca/metabolites/hmdb00095>, Nov. 16, 2005.*
International Preliminary Report on Patentability for PCT/NL2011/050168—dated Feb. 21, 2012.
International Search Report for PCT/NL2011/050168—dated May 3, 2011.
De Kort et al., "Calcium-binding Capacity of Organic and Inorganic Ortho- and Polyphosphates", Dairy Sci. Technolo. 89, 2009, pp. 283-299, 17 pages.
Dewan et al., "Viscosity and Voluminosity of Bovine Milk Casein Micelles", Department of Biochemistry,Department of Food Science and Industries, University of Minnesota, Jun. 30, 1972, pp. 699-705, 7 pages.
Eilers, "Colloidchemische Studen Aan Ondermelk", Verslagen Van Landbouwkundige Onderzoekingen No. 50 (15) G, pp. 97-103, 5 pages.
Eilers, "Die Viskosität von Emulsionen hochviskoser Stoffe als Funktion der Konzentration," Kolloid Z, 1941, 97(3)313-321.
Fox et al., "Gelation of Milk Solids by Orthophosphate", Dairy Products Laboratory, Eastern Utilization Research and Development Division Agricultural Research Service, USDA, Mar. 17, 1964, pp. 179-185, 7 pages.
Gaucher et al., "Physico-chemical Characterization of Phosphate-added Skim Milk", International Dairy Journal 17, 2007, pp. 1375-1383, 9 pages.
Griffin et al., "The Disaggregation of Calcium-depleted Casein Micelles", Eur. J. Biochem. 174, 1988, pp. 339-343, 5 pages.
Griffin et al., "Variation of the Viscosity of a Concentrated, Sterically Stabilized. Colloid: Effect of Ethanol on Casein Micelles of Bovine Milk", Journal of Colloid and Interface Science, vol. 28, No. 1, 1989, pp. 223-229, 7 pages.
Guo et al., "Casein Precipitation Equilibria in the Presence of Calcium Ions and Phosphates", Colloids and Surfaces B: Biointerfaces 29, 2003, pp. 297-307, 11 pages.
Hallstrom et al., "Rheological Properties of Ultrafiltered Skim Milk. II. Protein Voluminosity", Department of Food Technology, University of Lund Sweden, Milchwissenschaft 43 (2), 1988, pp. 95-97, 4 pages.

(Continued)

*Primary Examiner* — Sergio Coffa
(74) *Attorney, Agent, or Firm* — Gilberto M. Villacorta; Sunit Talapatra; Foley & Lardner LLP

(57) ABSTRACT

Medical dairy products are highly concentrated in proteins and minerals. Formulation of such products is challenging, since viscosities can easily increase during processing and storage. It was found that using one or more chelating agents selected from the group consisting of a phosphoric acid, citric acid, a soluble phosphate salt, a soluble citrate salt, or a mixture thereof, the viscosity and the transparency of an aqueous micellar casein composition, comprising 6 to 20 g/100 ml of micellar casein and having a pH of about 6 to 8 could be controlled independently of each other. It was found that products become more viscous after addition of phytate, citrate, or orthophosphate, and that the viscosity depends on concentration and type of phosphate. Addition of hexametaphosphate leads to gel formation. In contrast, high concentrations of uridine monophosphate can be added without significantly affecting the viscosity.

14 Claims, 8 Drawing Sheets

(56) References Cited

OTHER PUBLICATIONS

Figure 1:
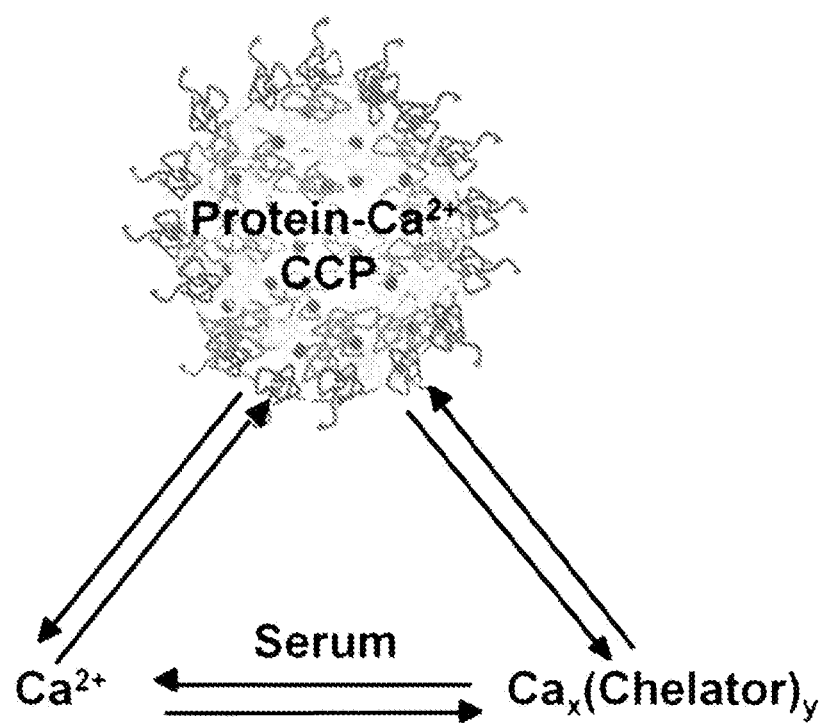

Harwalkar, "Age Gelation of Sterilized Milks", Food Research Institute, Agriculture Canada, Chapter 7, pp. 228-269, 23 pages.
Holt, "The Milk Salts and Their Interaction with Casein", Advanced Dairy Chemistry vol. 3, 1997, pp. 233-255, 15 pages.
Van Hooydonk et al., "PH-Induced Physico-Chemical Changes of Casein Micelles in Milk and Tehir Effect on Renneting. 1. Effect of Acidification on Physico-Chemical Properties", Neth. Milk Dairy J. 40, 1986, pp. 281-296, 10 pages.
Huppertz et al., "Biocompatible Micro-Gel Particles from Cross-Linked Casein Micelles", Biomacromolecules 2007, 8, pp. 1300-1305, 6 pages.
Karlsson et al., "Relataionship Between Physical Properties of Casein Micelles and Rheology of Skim Milk Concentrate," J. Dairy Sci., vol. 88, Nov. 1, 2005, pp. 3784-3797, 14 pages.
Kocak et al., "Controlling Age Gelation of UHT Milk With Additives", The Australian Journal of Dairy Technology, Jun. 1985, pp. 58-64, 8 pages.
Korolczuk, "Voluminosity and Viscosity of Casein Solution, I. The Correlation Between the Voluminosity, Protein Concentration and Viscosity", Milchwissenschaft 36 (7), 1981, pp. 414-416, 4 pages.
Krieger, "Rheology of Monodisperse Latices", Advances in Colloid and Interface Science 3, 1972, pp. 111-136, 26 pages.
Leviton et al., "High-Temperature-Short-Time Sterilized Evaporated Milk. IV. The Retardation of Gelation With Condensed Phosphates, Manganous Ions, Polyhydric Compounds, and Phosphatides", Dairy Products Laboratory, Utilization Research and Development Division, U.S. Dept.of Agriculture, Apr. 18, 1962, pp. 1045-1056, 12 pages.
Liang et al., "Effect of Phosphate on Bovine Casein Micelles (Behaviors of Bovine Casein Micelles under Various conditions Part III)", Laboratory of Food Chemistry, Collage of Agriculture, University of Osaka Prefecture, 1974, pp. 49-56, 8 pages.
Lin et al., "Effect of Calcium Ion on the Structure of Native Bovine Casein Micelles", Biochemistry, vol. 11, No. 10, 1971, pp. 1818-1821, 4 pages.
Marchin et al., "Effects of the Environmental Factors on the Casein Micelle Structure Studied by Cryo Transmission Electron Microscopy and Small-Angle X-Ray Scattering/Ultrasmall-Angle X-Ray Scattering", The Journal of Chemical Physics 126, 2007, 45101 1-10, 10 pages.
McMahon et al., "Supramolecular Structure of the Casein Micelle", J. Dairy Sci. 91, 2008, pp. 1709-1721, 13 pages.
Mekmene et al., "A Model for Predicting Salt Equilibria in Milk and Mineral-Enriched Milks", Food Chemistry 116, 2009, pp. 233-239, 7 pages.
Mizuno et al., "Effects of Emulsifying Salts on the Turbidity and Calcium-Phosphate-Protein Interactions in Casein Micelles", J. Dairy Sci. 88, 2005, pp. 3070-3078, 9 pages.
Mizuno et al., "Properties of Milk Protein Gels Formed by Phosphates", J. Dairy Sci. 90, 2007, pp. 4524-4531, 8 pages.
Morr, "Some Effects of Pyrophosphate and Citrate Ions Upon the Colloidal Caseinate-Phosphate Micelles and Ultrafiltrate of Raw and Heated Skimmilk", Department of Dairy Technology, The Ohio State University, Jan. 30, 1967, pp. 1038-1044, 7 pages.
Munyua et al., "The Influence of Ca2 on the Size and Light Scattering Properties of Casein Milcelles 1. Ca2 removal", Milchwissenschaft 35 (10), 1980, pp. 604-606, 4 pages.
Odagiri et al., "Complexing of Calcium by Hexametaphosphate, Oxalate, Citrate, and EDTA in Milk. I. Effects of Complexing Agents on Turbidity and Rennet Coagulation", Department of Food Science and Technology, University of California, Jun. 23, 1964, pp. 1306-1309, 4 pages.
Panouille et al., "Aggregation and Gelation of Casein Sub-Micelles", Food Colloids 2004: Interactions, Microstructure and Processing, pp. 194-209, 10 pages.
Philippe et al., "Physicochemical Characterization of Calcium-Supplemented Skim Milk", INRA, EDP Sciences, 2003, pp. 45-59, 9 pages.
Pitkowski et al., "Scattering and Turbidity of the Dissociation of Casein by Calcium Chelation", Biomacromolecules 2008, 9, pp. 369-375, 7 pages.
Smiddy et al., "Stability of Casein Micelles Cross-Linked by Transglutaminase", J. Dairy Sci. 89, 2006, pp. 1906-1914, 9 pages.
Snoeren et al., "The Viscosity of Skim-Milk Concentrates", Neth. Milk Dairy J. 36, 1982, pp. 305-316, 8 pages.
Sood et al., "Correlation Between Micelle Solvation and Calcium Content", New Zealand Journal of Dairy Science and Technology, 14, 1979, pp. 32-34, 4 pages.
Turner et al., "Inositol Phosphates in the Environment", Phil. Trans. R. Soc. Lond B, 357, 2002, pp. 449-469, 21 pages.
Udabage et al., "Mineral and Casein Equilibria in Milk: Effects of Added Salts and Calcium-Chelating Agents", Journal of Dairy Research 67, 2000, pp. 361-370, 10 pages.
Upreti et al., "Influence of Calcium and Phosphorus, Lactose, and Salt-to-Moisture Ratio on Cheddar Cheese Quality: pH Buffering Properties of Cheese", J. Dairy Sci. 89, 2006, pp. 938-950, 13 pages.
Van De Hulst, "Light Scattering by Small Particles", Leiden, the Netherlands, Mar. 1957, 6 pages.
Vujicic et al., "Interaction pf Polyphosphates ad Citrate with Skim-milk Proteins", Canadian Institute of Food Technology Journal, vol. 1, No. 1, Jan. 1968, pp. 17-21, 6 pages.
Walstra et al., "Dairy Science and Technology", Second Edition, 2006, 9 pages.
Ward et al., "EDTA-Induced Dissociation of Casein Micelles and its Effect on Foaming Properties of Milk", Journal of Dairy Research 64, 1997, pp. 495-504, 10 pages.
Zittle, "Precipitation of Casein from Aidic Solutions by Divalent Anions",Eastern REgional Research Laboratory, USDA, Jan. 3, 1966, pp. 361-364, 4 pages.

* cited by examiner

CONTROLLING THE TEXTURE OF HIGH-PROTEIN NUTRITIONAL COMPOSITIONS COMPRISING MICELLAR CASEIN

CROSS-REFERENCE TO RELATED APPLICATION(S)

This application is the National Phase of International Patent Application No. PCT/NL2011/050168, filed Mar. 11, 2011, published as WO 2011/112087, which claims priority to International Patent Application No. PCT/NL2010/050129, filed Mar. 11, 2010. The contents of these applications are herein incorporated by reference in their entirety.

FIELD OF THE INVENTION

The present invention is in the field of enteral nutritional compositions. More in particular, it relates to an aqueous micellar casein composition comprising 6 to 20 g of micellar casein per 100 ml of composition, and having a pH of about 6 to 8, as well as to an enteral nutritional composition comprising a high amount of micellar casein, and the problems of—independently—controlling viscosity, transparency and phosphate levels in such a composition.

BACKGROUND OF THE INVENTION

Preferably, medical dairy products are highly concentrated in nutrients, in particular in proteins and minerals, to meet the daily intake of nutrients in malnourished patients. These patients can be cachectic patients or persons suffering from end-stage AIDS, cancer or cancer treatment, severe pulmonary diseases like COPD (chronic obstructive pulmonary disease), tuberculosis and other infection diseases or persons that experienced severe surgery or trauma like burns. Furthermore, persons suffering from disorders in the throat or mouth such as oesophageal cancer or stomatitis and persons having problems with swallowing like dysphagic persons, require special liquid, low-volume nutrition. Also, persons just suffering from reduced appetite or loss of taste, will benefit from low-volume, preferably liquid, food. These patients can also be elderly persons, in particular frail elderly and elderly at risk of becoming frail. In this regard, although an elderly person's energy needs may be reduced, their ability to consume products may also be diminished. For example, they may have difficulty consuming a product due to, e.g., swallowing difficulties, or due to too large amount of product they need to consume to meet the daily intake of nutrients. Hence, compliance is not optimal, and often, the intake is suboptimal, leading to suboptimal nourishment, and in the end, to malnutrition.

The aforementioned groups of patients may be extremely sensitive to food consistency and to the organoleptic properties of the product such as, for instance viscosity, mouth feel, taste, smell and colour. Also, patients such as cachectic patients, typically suffer from extreme weakness which often prevents them from sitting in a vertical position and from drinking food from a carton or even to suck it from a straw. These patients benefit well from liquid low-volume enteral compositions with a high content of nutrients, in particular proteins.

However, high amounts of protein and minerals increase the overall viscosity of the product during processing and storage because of shifts in the protein-mineral equilibria. Low viscous liquid products, however, are mostly appreciated by patients, which makes it challenging to formulate such products.

Therefore, the problem underlying the present invention is to provide a liquid enteral composition for providing nutrition, either as a supplement, or as a complete nutrition, comprising a high content of an intact protein, in particular micellar casein, as major protein source, in the smallest volume of liquid, and which supports nutrition and well-being in the different patient groups mentioned above, in particular to an elderly person or an ill patient.

Casein micelles in concentrated milk interact more frequently with each other than in bovine milk because of the smaller distances between the micelles. Concentrated milk, therefore, behaves like a shear-thinning non-Newtonian fluid, which means that viscosity is dependent on shear rate (Karlsson et al., 2005). The viscosity of colloidal systems is, in general, dependent of the viscosity of the continuous phase, shape, and size distribution of particles, and of their mutual interactions together with assumptions on how the viscosity follows the volume fraction. The volume fraction ($\Phi$) of the casein micelles is a dimensionless number, defined as fraction of the total volume taken by the particles. It can be determined by measuring the viscosity ($\eta$) of the solution. Eilers (1945) generated formula (1) to estimate the viscosity of concentrated dairy systems.

$$\eta = \eta_0 \left( 1 + \frac{1.25\Phi}{1 - \Phi/\Phi_{max}} \right)^2 \quad (1)$$

$\eta_0$ represents the viscosity of the continuous phase and is 1 mPa·s. $\Phi_{max}$ represents the maximum packing volume fraction for which the viscosity tends to go to infinity. A value of 0.74 is normally used for $\Phi_{max}$ in a solution with spheres of similar sizes (Eilers, 1945), but for concentrated milk, in which the particles have various sizes, a value of 0.79 should be used. This formula is extended from the Einstein relation, which describes the viscosity of dispersions in very dilute systems, in which the particles are spherical and not deformable or affected by each other's presence (Dewan et al., 1972; Eilers, 1945; Karlsson et al., 2005).

Voluminosity is defined as the total volume occupied by a gram of protein and has been related to the volume fraction $\Phi$ of the proteins in the solution (Eilers, 1941) The voluminosity of the casein micelles is a determining factor for the viscosity of the solution. The voluminosity of casein micelles increases when the micelles become more hydrated (e.g. due to calcium depletion), which causes release of specific caseins from the micelle and expansion and swelling of the micelles. The order of specific casein release depends on the amount of phosphoserine residues and hence the specific sensitivity for calcium ions. When the micelles become more calcium depleted, more casein will be released from the casein micelle. As a result, the order of dissociation is β-casein>$\alpha_{s1}$-casein>$\alpha_{s2}$-casein (Holt, 1997). Although κ-casein has 0 or 1 phosphoserine residues, it will probably remain stacked into the casein micelle because of its hydrophobic interactions. For instance, the amount of β-casein that leaves the casein micelles increases with decreasing temperature and calcium content. The increase in size of the casein micelles is caused by expansion and swelling of the casein micelles, which is due to increase in electrostatic repulsion and osmosis of continuous phase in the micelles, respectively (Leviton and Pallansch, 1962). Moreover, the free calcium ions in the continuous phase reduce the electrostatic repulsion in the casein micelles, which keeps the micelles more compact.

The interactions between casein micelles in concentrated milk are strongly influenced by e.g. ionic strength, mineral content and composition, pH, and temperature (Karlsson et al., 2005). Phosphates and citrate, which are minerals that are frequently added to medical nutrition, processed cheese, or (concentrated) UHT milk, interact with casein micelles by binding calcium ions or by binding directly to the casein micelle (Kocak and Zadow, 1985; Mizuno and Lucey, 2005; Vujicic et al., 1968). In general, their calcium binding capacity can be ranked in the following order: long-chain phosphate > tripolyphosphate > pyrophosphate > citrate > orthophosphate (Zittle, 1966).

PRIOR ART

Although a large number of prior art literature is available (cited in the application, where appropriate), only few publications deal with liquid enteral nutritional compositions comprising high amounts of micellar casein, in the range of 6 to 20 g/100 ml of composition.

The effect of phosphates and citrate on physical changes of milk solutions is mainly studied in skim milk systems, where about 20% of the protein is whey, with low concentration factors (maximally ~6.5% w/v protein), and relatively low phosphate or citrate levels. Several of these studies focused on milk gels (Mizuno & Lucey, 2007) or on age gelation (Harwalkar, 1982; Kocak & Zadow, 1985; Leviton & Pallansch, 1962).

U.S. Pat. No. 5,683,984 discloses an enteral tube feeding composition with a native micellar casein protein component. Viscosity issues are identified, and tackled in WO 2009/072885, which discloses a high energy and high protein liquid nutrition enteral composition that contains micellar casein and caseinate, and optionally a small amount of whey.

Furthermore, a large number of publications deals with the turbidity effect of added phosphate salts on dairy products such as skimmed milk, however, none describe the effect of these salts on the viscosity in liquid enteral nutritional compositions comprising high amounts of micellar casein, in the range of 6 to 20 g/100 ml.

Liang et al. (Nippon Nogei Kagaku Kaishi (1974), 48(1), 49-56 describe the effects of glycerophosphate on gelation of casein micelles and on turbidity in skimmed milk (containing about 3 g/100 ml of casein micelles).

WO 01/72135 A1 (Australian Food Industry Science Center) and U.S. Pat. No. 6,455,082 B1 (Nestec) deal with the addition of phosphates to milk in order to stabilize the milk (containing about 3 g/100 ml of casein micelles). Although they disclose an effect on viscosity, they do not teach an effect on transparency, and certainly not in a high-protein system, which is much more critical than a low-protein system such as milk with regard to viscosity and transparency behaviour.

DETAILED DESCRIPTION OF THE INVENTION

The inventors have now found that by using one or more chelating agents selected from the group consisting of a phosphoric acid, citric acid, a soluble phosphate salt, a soluble citrate salt, or a mixture thereof, the viscosity and the transparency of an aqueous micellar casein composition, comprising 6 to 20 g/100 ml of micellar casein and having a pH of about 6 to 8, could be controlled independently of each other. The use of a chelating agent for independently controlling viscosity and transparency of an aqueous micellar composition is not known in the art.

In one embodiment, the composition comprises one or more chelating agents selected from the group consisting of a phosphoric acid, citric acid, a soluble phosphate salt, a soluble citrate salt, or a mixture thereof, with the proviso that citric acid, a soluble citrate salt or a mixture thereof is excluded as the sole chelating agent.

In one embodiment, the composition comprises one or more chelating agents selected from the group consisting of a phosphoric acid, a soluble phosphate salt, or a mixture thereof.

In one embodiment, the aqueous micellar casein composition does not, or not substantially, contain any one of fat, digestible and non-digestible carbohydrates. With "not substantially contain" it is intented that the contributions of these components is preferably less than 5 weight %, based on total dry matter of the composition.

Preferably, the use is effected by adding the chelating agents to the aqueous micellar casein composition.

With the wording "independently" is meant that the viscosity and transparency can be set to any value, independently of each other, by selecting the appropriate chelating agent with an appropriate concentration or any combination of more than one appropriate chelating agent with its appropriate concentration. In this way, it is possible to obtain both transparant and very viscous compositions, yet also very milky and very liquid compositions. This latter set of properties is very interesting and important for the development of nutritional compositions, in particular dairy-based medical nutrition, comprising high amounts of micellar casein, in particular comprising 6 to 20 g/100 ml of micellar casein.

With "soluble" it is intended to refer to a salt that is soluble in water at pH 6-8.

Preferably, the aquous micellar casein composition according to the invention comprises at least 6, 7, 8, 9, 10, 11, 12, 13, 14, 15, 16, 17, 18 or 19 g and at most 20 g of micellar casein per 100 ml of composition, preferably 11 to 18 g/100 ml, more preferably 12 to 18 g/100 ml, and most preferably 14 to 18 g/100 ml.

The pH of the aquous micellar casein composition should be between about 6 and 8. The pH is determined in the aquous micellar casein composition and this can be done by routine methods, known to the skilled person, such as using a commercially available pH metering device.

Furthermore, with the appropriate choice of chelating agent according to the invention, it is possible, independently of the viscosity and transparency, to add amounts of phosphorous (as a phosphoric acid or a phosphate) to an aqueous micellar casein composition, comprising 6 to 20 g/100 ml of micellar casein and having a pH of about 6 to 8.

Within the meaning of this application, the wording "transparency" is the inverse of the wording "turbidity". Turbidity is the name of the parameter measured in the experiments. This skilled person is familiar with the concept of turbidity (e.g. at 700 nm) using spectrophotometry dealing with caseins (Philippe et al., 2003).

Micellar casein, sometimes also referred to as "native" micellar casein, refers to casein in the form of micelles, which is the native form of casein in milk. It is a high quality milk protein and naturally occurring in milk in a concentration of about 2.6 g/100 ml (Dairy Science and Technology, Walstra et al., CRC Press, 2006). It is concentrated by a process that does not, or does not substantially denature the casein proteins and it is marketed as Micellar Casein Isolate (MCI). Fresh skim milk is subjected to a microfiltration process, in much the same process used to concentrate whey protein, to produce a pure, substantially undenatured milk protein with its native structure. The resulting material contains between 90% and 95%, preferably more than 95% by weight of micellar casein on dry matter, the rest mainly being whey protein and other non-protein nitrogen and other constituents, such as lactose and inorganic salts, in particular calcium phosphate. The casein micelles generally have a hydrodynamic radius of 40 to 400 nm, a molecular weight of 106 to 109 Dalton and a calcium: phosphorous weight ratio of 1.4 to 2.4, the calcium-content being very high, in the order of about 25 g/kg protein. It has an intrinsic low viscosity and a liquid composition comprising said MCI is therefore easy to drink. The amount of monovalent metal ions, in particular Na and K, is very low, typically in the range of about 1 to 2 g/kg protein.

In contrast, casein, as it is used in the context of this invention, refers to the curd form of casein, having lost its native micellar structure. It is bound to a metal, such as sodium, potassium, calcium and magnesium, and is commonly called caseinate.

Within the context of this invention, it is understood that micellar casein may also be provided by other milk protein sources, such as, for instance, sources with essentially preserve the natural 80:20 ratio of casein to whey, such as Milk Protein Concentrate (MPC), which is a powder product usually prepared by ultrafiltration with an average protein content of about 80 weight %, Milk Protein Isolate (MPI), a powder product usually prepared by precipitation with an average protein content of more than 85 weight %, and skimmed concentrated milk. The micellar casein may also be provided in liquid form via an ultrafiltrate or microfiltrate.

According to one embodiment, the phosphoric acid is selected from the group consisting of uridine monophosphoric acid, cytidine monophosphoric acid, orthophosphoric acid, inositol hexaphosphoric acid, hexametaphosphoric acid, or a mixture thereof, and the phosphate salt is selected from the group consisting of uridine monophosphate, cytidine monophosphate, orthophosphate, inositol hexaphosphate, hexametaphosphate, or a mixture thereof.

According to another embodiment, the soluble salt is a monovalent salt, preferably a sodium salt, a potassium salt, or a mixture thereof. These salts are preferred for the development of nutritional compositions as they introduce metals as counter ions (e.g. sodium or potassium) which are essential in a normal diet.

According to yet another embodiment, the counter ion (e.g. sodium or potassium) is present in an amount less than or equal to an equimolar amount, relative to the acid. For example, one molecule of inositol hexaphosphate may contain 1 to 12 counter ions, and the product inositol hexaphosphate may therefore contain molecules with different number of counter ions, such that the total equivalent of counter ions in the product is smaller than or equal to the total equivalent of inositol hexaphosphate.

According to yet another embodiment, the phosphate salt is selected from the group consisting of disodium uridine monophosphate ($Na_2UMP$, an organic orthophosphate), disodium cytidine monophosphate ($Na_2CMP$, an organic orthophosphate), disodium orthophosphate ($Na_2HPO_4$, an inorganic orthophosphate), sodium phytate, also called dodecasodium inositol hexaphosphate (SP, an organic polyphosphate), and (hexa)sodium hexametaphosphate (SHMP, an inorganic polyphosphate). Preferably, the citrate salt is trisodium citrate (TSC). It is understood that—in practice—a product does not always contain an equimolar amount of metal counter ions, relative to the acid, although the product is designated as such. Such products are also comprised within the definition of the phosphate and citrate salts according to the invention.

Preferably, the one or more chelating agents is selected from the group consisting of a phosphoric acid, a soluble phosphate salt, or a mixture thereof.

Most preferably, the phosphate salt is disodium uridine monophosphate or disodium cytidine monophosphate, preferably disodium uridine monophosphate. Using this salt, a liquid micellar casein composition is obtained with a substantially unaffected transparency and viscosity, yet providing the necessary phosphorous and counter ions for a nutritional composition.

The calcium binding capacity of the salts according to the invention is based on their number of charges. Their order in calcium binding capacity decreases from SP>SHMP>TSC=$Na_2HPO_4$>$Na_2UMP$=$Na_2CMP$. In addition, several of these phosphates have the ability to interact with the casein micelles. Free calcium and phosphate ions, calcium phosphate complexes, and calcium and phosphate ions incorporated in the casein micelles are in equilibrium with one another in dairy systems (FIG. 1). Addition of the chelating agents according to the invention will shift these equilibria, as they chelate calcium ions. As a result, this will affect the voluminosity of the casein micelles, because the micelles become more calcium depleted, the micelles may dissociate and specific caseins are released from the casein micelle.

The voluminosity might also decrease upon addition of, for example, calcium ions, because they will be incorporated in the casein micelles (Walstra et al., 2006). These changes in voluminosity both affect the viscosity and heat stability of milk systems at UHT conditions. Orthophosphate, for example, is naturally present in casein micelles as colloidal calcium phosphate (CCP). Addition of $Na_2HPO_4$ to milk causes binding of the phosphate ions with the calcium ions and calcium phosphate microcrystals will be formed. Reorganisation of the micellar structure and change in voluminosity will occur, because complexes, such as $Ca_3(PO_4)_2$, will be integrated in the casein micelles (Guo et al., 2003). $Na_2UMP$ has a weak calcium binding capacity (de Kort et al., 2009) and only slightly affects the voluminosity of casein micelles. $Na_2CMP$ shows similar behaviour. No information is available about the interaction of $Na_2UMP$ and $Na_2CMP$ with casein micelles. Polyphosphates, such as SHMP and SP, are highly anionic charged, which gives them the possibility to bind to the positively charged amino acids of the casein residues or CCP (Mizuno and Lucey, 2007; Vujicic et al., 1968; Zittle, 1966). Interaction of polyphosphates with casein micelles at neutral pH in (concentrated) milk creates extra net negative charges on the micelles, which causes expansion of the casein micelles (Leviton and Pallansch, 1962). SHMP increases the viscosity or even causes gelation in casein systems, because SHMP has the ability to cross-link casein micelles via interaction with CCP or amide groups (Kocak and Zadow, 1985; Mizuno and Lucey, 2007; Vujicic et al., 1968). Citrate does not bind or cross-link caseins (Mizuno and Lucey, 2005), but chelates calcium ions that were bound to the casein micelles. Citrate and the formed calcium citrate complexes remain as stable, soluble complexes in the serum phase (Mizuno and Lucey, 2007; Morr, 1967; Vujicic et al., 1968) or form insoluble calcium citrate crystals during storage. Addition of citrate results in an increase in hydration of casein micelles, swelling of the micelles measured as an increase in viscosity and transparency of the solutions (Morr, 1967). Transparency can be determined by measuring the turbidity of the solution with a spectrophotometer. It is an important tool to relate changes in ion, protein, and water distributions with the physicochemical properties of the solutions and, more specific, of the casein micelles (Philippe et al., 2003). The density and refractive index, for example, will change upon shrinkage, dissociation or swelling of the casein micelles.

The effect of ortho- and polyphosphates and citrate on physical properties of normal or concentrated skim milk has been studied (Mizuno and Lucey, 2007; Morr, 1967; Vujicic et al., 1968), but these systems contain whey protein and relatively low protein concentrations (maximal ~6.5 weight % caseinate). In addition, research focussed on preparation of milk gels with phosphates (Mizuno and Lucey, 2007) or on acceleration or retardation of age gelation after addition of phosphates or citrate (Harwalkar, 1982; Kocak and Zadow, 1985; Leviton and Pallansch, 1962). Also, relatively low phosphate or citrate concentrations were used in these studies.

The amount of chelating agent should be chosen in accordance with the invention, but it was shown that the addition of 1 to 120 $mEq \cdot L^{-1}$ of said chelating agent, preferably 5 to 100 $mEq \cdot L^{-1}$, more 10 to 80 $mEq \cdot L^{-1}$, most preferably 20 to 60 $mEq \cdot L^{-1}$ of said chelating agent is sufficient for obtaining the claimed effects.

Figure 3:
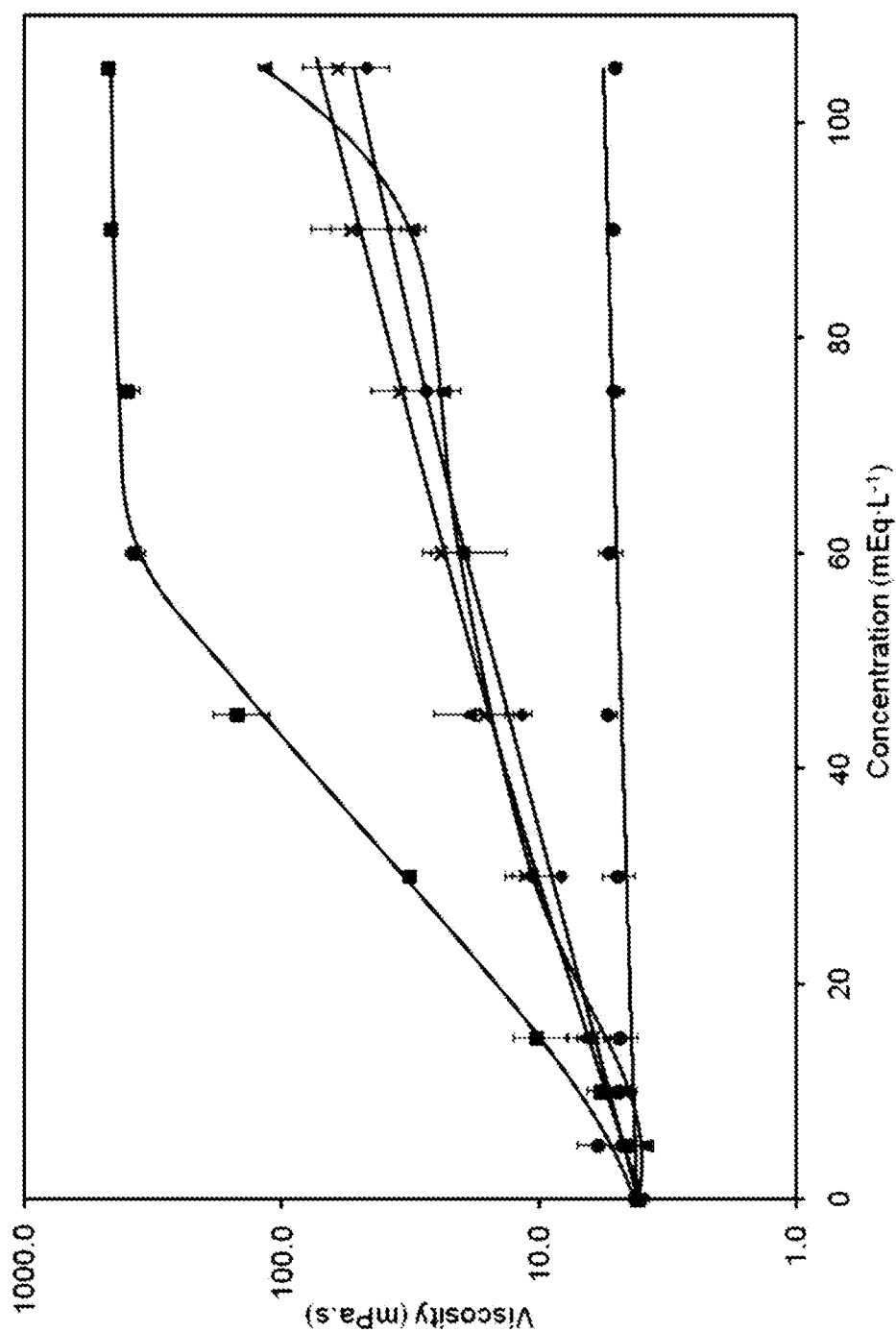
Figure 8:
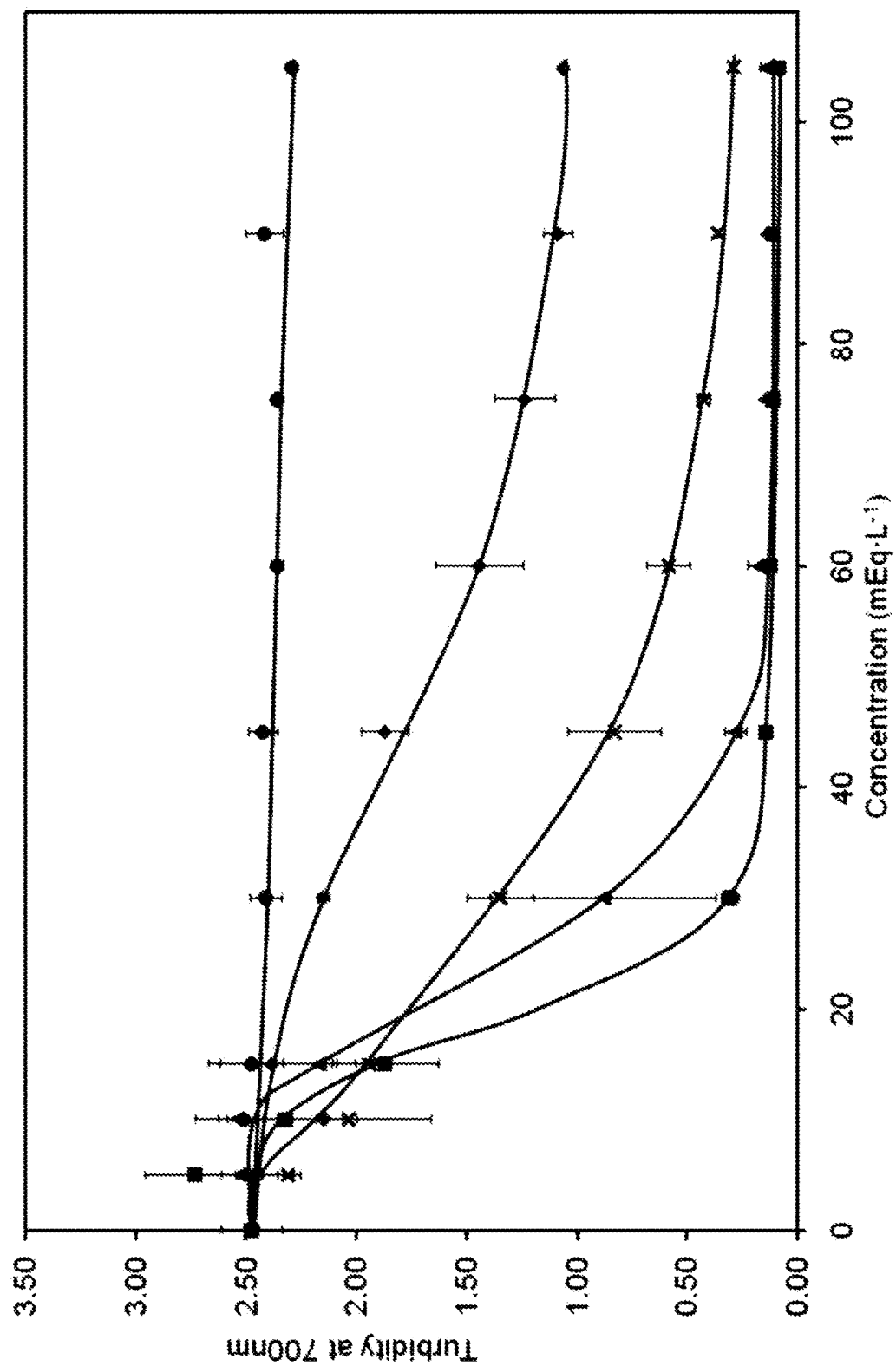

By using a chelating agent according to the invention, three types of compositions can be produced (FIG. 3 in combination with FIG. 8). It was found that a composition becomes more viscous after addition of inositol hexaphosphate (such as SP), citrate (such as TSC), or an inorganic orthophosphate (such as $Na_2HPO_4$), and that the viscosity depends on concentration and type of phosphate and citrate. Addition of hexametaphosphate (such as SHMP) leads to highly viscous and transparent compositions and even gel formation. In contrast, high concentrations of uridine monophosphate (such as $Na_2UMP$) can be added without significantly affecting the viscosity and hardly changing the initial transparency of the composition.

By using two or more chelating agents according to the invention, any type of compositions can be produced, having any desired viscosity, transparency and phosphorous content.

Nutritional Composition

In a preferred embodiment, the invention is directed to a nutritional composition comprising 9 to 20 g of protein per 100 ml of the composition and having a pH of about 6 to 8, in which all or a major part of said protein comprises micellar casein, comprising one or more chelating agents selected from the group consisting of a phosphoric acid, citric acid, a soluble phosphate salt, a soluble citrate salt, or a mixture thereof, as well as to a number of preferred embodiments as claimed in the appended claims. The amount of chelating agent could be chosen in accordance with the invention; the composition preferably comprises 1 to 120 $mEq \cdot L^{-1}$ of said chelating agent, preferably 5 to 100 $mEq \cdot L^{-1}$, more 10 to 80 $mEq \cdot L^{-1}$, most preferably 20 to 60 $mEq \cdot L^{-1}$ of said chelating agents.

In a preferred embodiment, the composition comprises one or more chelating agents selected from the group consisting of a phosphoric acid, citric acid, a soluble phosphate salt, a soluble citrate salt, or a mixture thereof, with the proviso that citric acid, a soluble citrate salt or a mixture thereof is excluded as the sole chelating agent.

In a preferred embodiment, the nutritional composition comprises one or more chelating agents selected from the group consisting of a phosphoric acid, a soluble phosphate salt, or a mixture thereof.

Preferably, the nutritional composition according to the invention comprises at least 9, 10, 11, 12, 13, 14, 15, 16, 17, 18 or 19 g and at most 20 g of protein per 100 ml of composition, preferably 11 to 18 g/100 ml, more preferably 12 to 18 g/100 ml, and most preferably 14 to 18 g/100 ml, in which all or a major part of said protein comprises micellar casein.

In the context of this application, the wording "all or major part" in relation to micellar casein should be interpreted as an amount of micellar casein which ranges from 70 to 100% of the total protein.

According to another embodiment of the present invention, the nutritional composition of the invention comprises optionally at most 30 weight % of caseinate, based on the total weight of the protein.

According to another embodiment of the present invention, the protein provides 10% to 100%, preferably 20% to 80%, more preferably 30% to 70%, most preferably 30% to 60% of the total energy content of the composition. The high levels of protein are beneficial for patients who may not be physically capable of receiving a large volume, for example, fluid restricted patients. Such patients can be given a reduced level of fluid while still receiving a required amount of nutritional support per day. The composition may be used as a complete nutrition, in addition to or as a replacement for a normal meal consumption. The composition may also be used as a supplement, in addition to normal meal consumption, when the uptake of fats and carbohydrates is of less concern.

According to another embodiment of the present invention, the nutritional composition has an energy density of at least 0.36 kcal/ml, more preferably at least 1.0 kcal/ml, particularly at least 1.5 kcal/ml of composition, more in particular at least 2.0 kcal/ml.

Although the composition has a high energy density, by choosing the appropriate chelating agents according to the invention, it may also have a sufficiently low viscosity to allow it to be consumed by persons that may have difficulty swallowing products or those that are tube fed. Hence, in one embodiment, the nutritional composition is a liquid, preferably having a viscosity of less than 200 mPa·s, preferably less than 80 mPa·s, preferably less than 70 mPa·s, more preferably 50 mPa·s, still more preferably less than 40 mPa·s, most preferably equal to about 20 mPa·s.

In one embodiment of the present invention, the amount of micellar casein in the nutritional composition according to the invention is at least 70 weight %, preferably at least 80 weight %, more preferably at least 90 weight %, more preferably at least 95 weight % and at most 100 weight % of the total protein present in the nutritional composition.

As aforementioned, the nutritional composition of the present invention should not contain large amounts of proteins other than micellar casein and, according to one embodiment, optionally at most 30 weight % of caseinate. In a further embodiment of the present invention, the nutritional composition may comprise up to about 15 weight % of whey, preferably less than or equal to 10 weight % of whey, more preferably 1 to 10 wt % of the total protein present in the nutritional composition; in one embodiment, the composition comprises less than or equal to 5 weight % of whey of the total protein present in the nutritional composition.

In one embodiment of the present invention, the weight ratio of micellar casein to caseinate ranges from about 100:0 to about 70:30. Preferably, the weight ratio of micellar casein to caseinate ranges from about 80:20 to about 100:0.

The nutritional composition according to the invention is designed to either supplement a person's diet or to provide complete nutritional support. Hence, the composition according to the invention may further comprise at least fat and/or carbohydrate and/or a source of vitamins, minerals, trace elements and/or a source of indigestible carbohydrates. Preferably, the composition according the invention is a nutritionally complete composition.

In one embodiment, the invention pertains to a method of providing nutrition to a person in need thereof, comprising the steps of administering to said person the nutritional composition as described here. The person is preferably an elderly person, a person that is in a disease state, a person that is recovering from a disease state, a person that is malnourished, or a healthy person such as a sportsman or sportswoman or an active elderly. In this respect, it is submitted that in the context of this application, an elderly person is a person of the age of 50 or more, in particular of the age of 55 or more, more in particular of the age of 60 or more, more in particular of the age of 65 or more.

Fat

In one embodiment the present enteral nutritional composition further comprises fat. The amount of fat may range between 5 and 95%, preferably between 10 and 70%, more preferably between 20 and 40%, relative to the total energy content of the composition.

With regard to the type of fat, a wide choice is possible, as long as the fat is of food quality. The fat may either be an animal fat or a vegetable fat or both. Although animal fats such as lard or butter have essentially equal caloric and nutritional values and can be used interchangeably, vegetable oils are highly preferred in the practice of the present invention due to their readily availability, ease of formulation, absence of cholesterol and lower concentration of saturated fatty acids. In one embodiment, the present composition comprises rapeseed oil, corn oil and/or sunflower oil.

The fat may include a source of medium chain fatty acids, such as medium chain triglycerides (MCT, mainly 8 to 10 carbon atoms long), a source of long chain fatty acids, such as long chain triglycerides (LCT) and phospholipid-bound fatty acids such as phospholipid-bound EPA or DHA, or any combination of the two types of sources. MCTs are beneficial because they are easily absorbed and metabolized in a metabolically-stressed patient. Moreover, the use of MCTs will reduce the risk of nutrient malabsorption. LCT sources, such as canola oil, rapeseed oil, sunflower oil, soybean oil, olive oil, coconut oil, palm oil, linseed oil, marine oil or corn oil are beneficial because it is known that LCTs may modulate the immune response in the human body.

In one specific embodiment, the fat comprises 30 to 60 weight % of animal, algal or fungal fat, 40 to 70 weight % of vegetable fat and optionally 0 to 20 weight % of MCTs based on total fat of the composition. The animal fat preferably comprises a low amount of milk fat, i.e. lower than 6 weight %, especially lower than 3 weight % based on total fat. In particular, a mixture of corn oil, egg oil, and/or canola oil and specific amounts of marine oil is used. Egg oils, fish oils and algal oils are a preferred source of non-vegetable fats. Especially for compositions that are to be consumed orally, in order to prevent formation of off-flavours and to decrease a fishy after-taste, it is recommended to select ingredients that are relatively low in docosahexaenoic acid (DHA), i.e. less than 6 weight %, preferably less than 4 weight % based on total fat. Marine oils containing DHA are preferably present in the composition according to the invention in an amount lower than 25 weight %, preferably lower than 15 weight % based on total fat. On the other hand, inclusion of eicosapentaenoic acid (EPA) is highly desirable for obtaining the maximum health effect. Therefore, in another embodiment, the amount of EPA may range between 4 weight % and 15 weight %, more preferably between 8 weight % and 13 weight % based on total fat. The weight ratio EPA:DHA is advantageously at least 6:4, for example between 2:1 and 10:1. In yet another embodiment, the amount of EPA is very low, such as 0.1 to 1 weight %, preferably 0.3 weight % or 0.6 weight %, based on total fat.

Also, the nutritional composition according to the invention may beneficially comprise an emulsifier. Commonly known emulsifiers may be used and generally the emulsifier contributes to the energy content of the fat in said composition.

Digestible Carbohydrate

In one embodiment of the present invention, the nutritional composition according to the invention further comprises a digestible carbohydrate. Preferably, the digestible carbohydrate provides between 30 to 60% of the total energy content of the composition according to the invention. The digestible carbohydrate may comprise either simple or complex carbohydrates, or any mixture thereof. Suitable for use in the present invention are glucose, fructose, sucrose, lactose, trehalose, palatinose, corn syrup, malt, maltose, isomaltose, partially hydrolysed corn starch, maltodextrins, glucose oligo- and poly-saccharides.

The composition of the digestible carbohydrate preferably is such that high viscosities, excessive sweetness, excessive browning (Maillard reactions) and excessive osmolarities are avoided. Acceptable viscosities and osmolarities may be achieved by adjusting the average chain length (average degree of polymerisation, DP) of the digestible carbohydrates between 1.5 and 6, preferably between 1.8 and 4. In order to avoid excessive sweetness, the total level of sucrose and fructose is preferably less than 60%, more preferably less than 52%, more preferably less than 40% of the weight of the carbohydrate, especially of the digestible carbohydrate. Long-chain digestible carbohydrates such as starch, starch fractions and mild starch hydrolysates (DE>1, DE<20), may also be present, preferably in an amount of less than 25 weight %, especially less than 15 weight % of the digestible carbohydrate, and less than 6 g/100 ml, preferably less than 4 g/100 ml of the total enteral composition according to the invention.

In one embodiment of the present invention, the digestible carbohydrate includes maltodextrose with a high DE (dextrose equivalent). In one embodiment the digestible carbohydrate includes maltodextrose with a DE of >10, preferably a DE of >20, more preferably >30 or even >40, such as a DE of about 47. In one embodiment of the present invention, the digestible carbohydrate includes maltodextrose with a DE >10 and sucrose.

Surprisingly, the use of maltodextrose leads to few or no Maillard reaction products upon heating. Without being bound to any explanation, this effect might be attributed to the fact that the compact micellar structure of the micellar casein offers few lysine reaction sites for a Maillard reaction. In one embodiment of the present invention, the digestible carbohydrate includes maltodextrose with a high DE in an amount of at least 35 weight %, preferably at least 50 weight %, preferably at least 65 weight %, preferably at least 90 weight % of the total weight of digestible carbohydrate. In one embodiment of the present invention, the digestible carbohydrate includes maltodextrose with a low DE of 2 to 20. In one embodiment of the present invention, the digestible carbohydrate includes maltodextrose with a low DE of 2 to 10, preferably with a low DE of about 2. In one embodiment of the present invention, the digestible carbohydrate includes maltodextrose with a low DE in an amount of less than 35 weight %, preferably less than 20 weight %, preferably less than 10 weight % of the digestible carbohydrate. Maltodextrose with a low DE may also be referred to as maltodextrine. In another embodiment of the present invention, the digestible carbohydrate includes maltodextrose with a high DE, preferably a DE of >20, preferably >30 or even >40, most preferably a DE of about 47 in combination with maltodextrose with a low DE, preferably a low DE of 2 to 20, more preferably a low DE of 2 to 10, most preferably with a low DE of about 2. As is known, maltodextrose with a low DE, such as of about 2, gives rise to a high viscosity. Maltodextrose with a high DE, such as of about 47 gives rise to a low viscosity, but is very sweet. The combination of both maltodextroses optimizes the balance between sweetness and viscosity. In one embodiment of the present invention, the digestible carbohydrate includes at least 65 weight %, preferably at least 90 weight %, based on total weight of digestible carbohydrate of maltodextrose with a DE>40, preferably with a DE of about 47 and 0 to 10 weight % of maltodextrose with a DE 2 to 10, preferably with a DE of about 2.

In another embodiment of the present invention, the digestible carbohydrate includes trehalose. It is one of the main objects of the invention to provide a nutritional composition with a low viscosity. Sucrose is very well suited for such purpose, but gives rise to very sweet compositions, which are in general disliked by the consumer. Maltodextrose with a low DE, such as of about 2, does not suffer from the latter drawback, but gives rise to a high viscosity. Maltodextrose with a high DE, such as of about 47 gives rise to a low viscosity, but is again very sweet, and gives further rise to the undesired Maillard reactions. Trehalose is a preferred choice of carbohydrate, as it gives rise to a low viscosity, no undesired Maillard reactions and it has a sweetness about half of that of sucrose. In one embodiment of the present invention, the digestible carbohydrate includes trehalose in an amount of 20% to 60% of the weight of the carbohydrate, in an amount of 20% to 45%, more preferably in an amount of 25% to 45% of the weight of the digestible carbohydrate.

Vitamins, Minerals and Trace Elements

The composition according to the invention may contain a variety of vitamins, minerals and trace elements.

In one embodiment of the present invention, the composition according to the invention provides all necessary vitamins, most of the minerals and trace elements. For example, the composition according to the invention preferably provides 6 mg of zinc per 100 ml of the composition which is beneficial for tissue repair in a healing patient. Preferably, the composition according to the invention (also) provides 25 mg of vitamin C per 100 ml of the composition to aid patients with more severe healing requirements. Further, preferably, the composition according to the invention (also) provides 2.25 mg iron per 100 ml of the composition. Iron is beneficial in maintaining bodily fluids as well as circulatory system functions in an elderly patient.

The invention implicates that a composition according to the present invention may contain sodium and/or potassium levels outside FSMP (Foods for Special Medical Purposes) legislation levels.

Non-digestible Carbohydrates

The enteral nutritional composition according to the invention may optionally be fortified with non-digestible carbohydrates (dietary fibres) such as fructooligosaccharides or inulin. In an embodiment of the present invention, the composition according to the invention comprises 0.5 g/100 ml to 6 g/100 ml of non-digestible carbohydrates. The dietary fibres include non-digestible oligosaccharides having a DP of 2 to 20, preferably 2 to 10. More preferably, these oligosaccharides do not contain substantial amounts (less than 5 weight %) of saccharides outside these DP ranges, and they are soluble. These oligosaccharides may comprise fructo-oligosaccharides (FOS), trans-galacto-oligosaccharides (TOS), xylo-oligosaccharides (XOS), soy oligosaccharides, and the like. Optionally, also higher molecular weight compounds such as inulin, soy polysaccharides, acacia polysaccharides (acacia fibre or arabic gum), cellulose, resistant starch and the like may be incorporated in the composition according to the invention. The amount of insoluble fibre such as cellulose is preferably lower than 20 weight % of the dietary fibre fraction of the composition according to the invention, and/or below 0.6 g/100 ml. The amount of thickening polysaccharides such as carrageenans, xanthans, pectins, galactomannans and other high molecular weight (DP>50) indigestible polysaccharides is preferably low, i.e. less than 20% of the weight of the fibre fraction, or less than 1 g/100 ml. Instead, hydrolysed polysaccharides such as hydrolysed pectins and galactomannans can advantageously be included.

A preferred fibre component is an indigestible oligosaccharide with a chain length (DP) of 2 to 10, for example Fibersol® (resistant oligoglucose), in particular hydrogenated Fibersol®, or a mixture of oligosaccharides having a DP of 2 to 10, such as fructo-oligosaccharides or galacto-oligosaccharides, which may also contain a small amount of higher saccharides (e.g. with a DP of 11 to 20). Such oligosaccharides preferably comprise 50 weight % to 90 weight % of the fibre fraction, or 0.5 g/100 ml to 3 g/100 ml of the composition according to the invention. Other suitable fibre components include saccharides that have only partial digestibility.

In a particular embodiment, the composition according to the invention comprises one or more of fructo-oligosaccharides, inulin, acacia polysaccharides, soy polysaccharides, cellulose and resistant starch.

In another embodiment of the present invention, the composition according to the invention may comprise a mixture of neutral and acid oligosaccharides as disclosed in WO 2005/039597 (N.V. Nutricia), which is incorporated herein by reference in its entirety. More in particular, the acid oligosaccharide has a degree of polymerization (DP) between 1 and 5000, preferably between 1 and 1000, more preferably between 2 and 250, even more preferably between 2 and 50, most preferably between 2 and 10. If a mixture of acid oligosaccharides with different degrees of polymerization is used, the average DP of the acid oligosaccharide mixture is preferably between 2 and 1000, more preferably between 3 and 250, even more preferably between 3 and 50. The acid oligosaccharide may be a homogeneous or heterogeneous carbohydrate. The acid oligosaccharides may be prepared from pectin, pectate, alginate, chondroitine, hyaluronic acids, heparin, heparane, bacterial carbohydrates, sialoglycans, fucoidan, fucooligosaccharides or carrageenan, and are preferably prepared from pectin or alginate. The acid oligosaccharides may be prepared by the methods described in WO 01/60378, which is hereby incorporated by reference. The acid oligosaccharide is preferably prepared from high methoxylated pectin, which is characterized by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). The acid oligosaccharides are preferably characterized by a degree of methoxylation above 20%, preferably above 50% even more preferably above 70%. Preferably the acid oligosaccharides have a degree of methylation above 20%, preferably above 50% even more preferably above 70%. The acid oligosaccharide is preferably administered in an amount of between 10 mg and 100 gram per day, preferably between 100 mg and 50 grams per day, even more between 0.5 and 20 gram per day.

The term neutral oligosaccharides as used in the present invention refers to saccharides which have a degree of polymerization of monose units exceeding 2, more preferably exceeding 3, even more preferably exceeding 4, most preferably exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term neutral oligosaccharides as used in the present invention preferably refers to saccharides which have a degree of polymerization of the oligosaccharide below 60 monose units, preferably below 40, even more preferably below 20, most preferably below 10. The term monose units refers to units having a closed ring structure, preferably hexose, e.g. the pyranose or furanose forms. The neutral oligosaccharide preferably comprises at least 90%, more preferably at least 95% monose units selected from the group consisting of mannose, arabinose, fructose, fucose, rhamnose, galactose, □-D-galactopyranose, ribose, glucose, xylose and derivatives thereof, calculated on the total number of monose units contained therein. Suitable neutral oligosaccharides are preferably fermented by the gut flora. Preferably the oligosaccharide is selected from the group consisting of: cellobiose (4-O-β-D-glucopyranosyl-D-glucose), cellodextrins ((4-O-β-D-glucopyranosyl)$_n$-D-glucose), B-cyclodextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructofuranoside), D-agatose, D-lyxo-hexylose, lactosucrose (O-β-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-α-D-glucopyranosyl-β-D-fructofuranoside), β-galactooligosaccharides or transgalacto-oligosaccharides (β-D-galactopyranosyl-(1-6)[β-D-glucopyranosyl]$_n$-(1-4)α-D glucose), lactulose (4-O-β-D-galactopyranosyl-D-fructose), 4'-galatosyllactose (O-D-galactopyranosyl-(1-4)-O-β-D-glucopyranosyl-(1-4)-D-glucopyranose), synthetic galactooligosaccharides (neogalactobiose, isogalactobiose, galsucrose, isolactose I, II and III), fructans—Levan-type (β-D-(2→6)-fructofuranosyl)$_n$ α-D-glucopyranoside), fructans— Inulin-type (β-D-((2→1)-fructofuranosyl)$_n$ α-D-glucopyranoside), 1 f-β-fructofuranosylnystose (β-D-((2→1)-fructofuranosyl)$_n$ B-D-fructofuranoside), xylooligosaccharides (B-D-((1→4)-xylose)$_n$, lafinose, lactosucrose and arabinooligosaccharides.

According to a further preferred embodiment the neutral oligosaccharide is selected from the group consisting of fructans, fructooligosaccharides, indigestible dextrins galactooligosaccharides (including transgalactooligosaccharides), xylooligosaccharides, arabinooligosaccharides, glucooligosaccharides, mannooligosaccharides, fucooligosaccharides and mixtures thereof. Most preferably, the neutral oligosaccharide is selected from the group consisting of fructooligosaccharides, galactooligosaccharides and transgalactooligosaccharides.

Suitable oligosaccharides and their production methods are further described in Laere K. J. M. (Laere, K. J. M., Degradation of structurally different non-digestible oligosaccharides by intestinal bacteria: glycosylhydrolases of Bi. adolescentis. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes. Numerous other commercial sources of indigestible oligosaccharides are readily available and known to skilled person. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment, the composition according to the invention comprises an acid oligosaccharide with a DP between 2 and 250, prepared from pectin, alginate, and mixtures thereof; and a neutral oligosaccharide, selected from the group consisting of fructans, fructooligosaccharides, indigestible dextrins, galactooligosaccharides including transgalactooligosaccharides, xylooligosaccharides, arabinooligosaccharides, glucooligosaccharides, mannooligosaccharides, fucooligosaccharides, and mixtures thereof.

In a further preferred embodiment the composition according to the invention comprises two chemically distinct neutral oligosaccharides. It was found that the administration of acid oligosaccharides combined with two chemically distinct neutral oligosaccharides provides an optimal synergistic immune stimulatory effect.
Preferably the composition according to the invention comprises:
    an acid oligosaccharides as defined above;
    a galactose-based neutral oligosaccharide (of which more than 50% of the monose units are galactose units), preferably selected from the group consisting of galactooligosaccharide and transgalactooligosaccharide; and
    a fructose and/or glucose based neutral oligosaccharide (of which more than 50% of the monose units are fructose and/or glucose, preferably fructose units), preferably inulin, fructan and/or fructooligosaccharide, most preferably long chain fructooligosaccharide (with an average DP of 10 to 60).

The mixture of acid- and neutral oligosaccharides is preferably administered in an amount of between 10 mg and 100 gram per day, preferably between 100 mg and 25 grams per day, even more preferably between 0.5 and 20 gram per day.

Viscosity and Osmolarity

In the context of this invention, the viscosity is measured in a rotational rheometer using a cup-and-bob geometry at 20° C. at a shear rate of 50 $s^{-1}$.

In one embodiment of the present invention, the viscosity of the enteral nutritional composition is less than 200 mPa·s, more preferably less than 150 mPa·s, more preferably less than 120 mPa·s, more preferably less than 100 mPa·s, more preferably less than 80 mPa·s, and most preferably 50 mPa·s. A low viscosity is ideal for orally administering the liquid enteral nutritional composition according to the invention because a person may easily consume a serving having a low viscosity such as that displayed by the present invention. This is also ideal for unit dosages that are tube fed.

In another embodiment of the present invention, the viscosity of the enteral nutritional composition is more than 200 mPa·s, more preferably more than 400 mPa·s, more preferably more than 600 mPa·s. A high viscosity is ideal for producing a pudding, a gel, or a semi-solid or semi-liquid composition. This is also ideal for unit dosages that are spoonable.

In one embodiment of the present invention, the osmolarity of the composition is preferably lower than 1200 mOsm/l, more preferably lower than 900 mOsm/l, more preferably lower than 800 mOsm/l, and most preferable lower than 700 mOsm/l.

Dosage Unit

The enteral nutritional composition according to the invention may have the form of a complete food, i.e. it can meet all nutritional needs of the user. As such, it preferably contains 1200 to 2500 kcal per daily dosage. The daily dosage amounts are given with respect to a daily energy supply of 2000 kcal to a healthy adult having a body weight of 70 kg. For persons of different condition and different body weight, the levels should be adapted accordingly. It is understood that the average daily energy intake preferably is about 2000 kcal. The complete food can be in the form of multiple dosage units, e.g. from 4 (250 ml/unit) to 40 (20 ml/unit) per day for an energy supply of 2000 kcal/day using a enteral nutritional composition according to the invention of 2.0 kcal/ml.

The enteral nutritional composition can also be a food supplement, for example to be used in addition to a non-medical food. Preferably as a supplement, the enteral nutritional composition contains per daily dosage less than 1500 kcal, in particular as a supplement, the enteral nutritional composition contains 400 to 1000 kcal per daily dose. The food supplement can be in the form of multiple dosage units, e.g. from 2 (250 ml/unit) to 10 (50 ml/unit) per day for an energy supply of 1000 kcal/day using a enteral nutritional composition according to the invention of 2.0 kcal/ml.

In one embodiment of the present invention, a unit dosage comprises any amount of the enteral nutritional composition according to the invention between 10 ml and 250 ml, the end values of this range included, preferably any amount between 25 ml and 200 ml, the end values of this range included, more preferably any amount between 50 ml and 150 ml, the end values of this range included, most preferably about 125 ml. For example, a person receiving 50 ml unit dosages can be given 10 unit dosages per day to provide nutritional support using a enteral nutritional composition according to the invention of 2.0 kcal/ml. Alternatively a person receiving 125 ml unit dosages can be given 4 or 5 or 6 or 7 or 8 unit dosages per day to provide nutritional support using a enteral nutritional composition according to the invention of 2.0 kcal/ml. Such small dosage units are preferred because of better compliance.

In one embodiment of the present invention, the composition is provided in a ready to use form and does not require reconstitution or mixing prior to use. The composition according to the invention can be tube fed or administered orally. For example, the composition according to the invention can be provided in a can, on spike, and hang bag. However, a composition may be provided to a person in need thereof in powder form, suitable for reconstitution using an aqueous solution or water such that the composition according to the invention is produced. Thus in one embodiment of the present invention, the present composition is in the form of a powder, accompanied with instructions to dissolve or reconstitute in an aqueous composition or water to arrive at the nutritional enteral composition according to the present invention. In one embodiment of the present invention, the present nutritional enteral composition may thus be obtained by dissolving or reconstituting a powder, preferably in an aqueous composition, in particular water.

In one embodiment of the present invention, the composition according to the invention may be used as a basis for the manufacturing of a semi-solid nutritional composition, such as a crème, a pudding, a custard, a soup, an ice cream, or a jelly. To this end, the composition according to the invention is processed to convert the low viscosity composition according to the invention into a more sold or viscous one, e.g. by adding thickeners or gelling agents and further process the mixture into the final product. Thickeners and/or gelling agents can also be present in the formulation from a more earlier stage of the process, or even dissolved together with the nutrients at the beginning of the process.

In one embodiment of the present invention, the composition according to the invention is packaged. The packaging may have any suitable form, for example a block-shaped carton, e.g. to be emptied with a straw; a carton or plastic beaker with removable cover; a small-sized bottle for example for the 80 ml to 200 ml range, and small cups for example for the 10 ml to 30 ml range. Another suitable packaging mode is inclusion of small volumes of (e.g. 10 ml to 20 ml) in edible solid or semi-solid hulls or capsules, for example gelatine-like coverings and the like. Another suitable packaging mode is a powder in a container, e.g. a sachet, preferably with instructions to dissolve or reconstitute in an aqueous composition or water.

EXPERIMENTAL

The following serves to evidence the inventive concepts. However, the invention is not considered tied by any of the theories and hypotheses for explaining the observed phenomena given here below.

The use of simplified concentrated milk systems, instead of complete medical nutrition recipes (i.e. systems containing high concentrations of mono- and divalent ions, carbohydrates, and fat), is an effective way to determine the influence of phosphates and citrate on the voluminosity of casein micelles. We have selected a commercial protein source, namely micellar casein isolate (MCI), which contains a negligible amount of whey protein, and prepared 9% w/v high-protein solutions to which phosphate and citrate in a large concentration range were added. In this application, we disclose the effect of ortho- and polyphosphates and citrate on the voluminosity of casein micelles. Viscosity and ultracentrifugation measurements were done to investigate changes in the total solution and voluminosity of the casein micelles, whereas turbidity and calcium-ion activity measurements were done to investigate changes inside the casein micelles. In this specification, we only use the terms swelling or shrinkage or dissociation of the micelles and not specific casein release when we discuss the change in voluminosity of the casein micelles, as specific casein release was not determined in this study.

Materials and Methods

Sample Preparation

To prepare a solution of 9% w/v micellar casein isolate, MCI (Nutripro™, DairyGold Food Ingredients, Cork, Ireland), protein powder was dissolved in 80% of the total demineralised water at ambient temperature, while stirring at 600 rpm with a laboratory stirrer (RW 20·n, IKA Labortechnik, Staufen, Germany). A 9% w/v MCI solution contains approximately 8.5 mmol·L$^{-1}$ sodium, 4.2 mmol·L$^{-1}$ potassium, 2.5 mmol·L$^{-1}$ chloride, 59.8 mmol·L$^{-1}$ calcium, 43.5 mmol·L$^{-1}$ phosphorus, and 3.1 mmol·L$^{-1}$ magnesium. The protein solution was homogenised with a high pressure laboratory homogeniser (NS2006L, GEA Niro Soari S.P.A., Parma, Italy) at 350+50 bar to obtain single casein micelles with a diameter $D_{[4,3]}$ of 0.15 µm as determined with a Mastersizer 2000 containing a hydro 2000G water bath (Malvern Instruments, Worcestershire, England). The temperature of the protein solution was 40° C. after homogenization.

Subsequently, concentration ranges of 0-105 mEq·L$^{-1}$ disodium uridine monophosphate (Yamasa Corporation, Chiba, Japan), disodium hydrogen phosphate (Merck & Co. Inc, Darmstadt, Germany), sodium hexametaphosphate (VWR International Ltd, Poole, England), phytic acid dodecasodium salt hydrate (Sigma-Aldrich GmbH, Steinheim, Germany), or trisodium citrate (Gadot Biochemical Industries Ltd., Haifa Bay, Israel) were added. Concentrations were based on milliequivalents of the phosphates and citrate to add a similar amount of charges to the samples. Only sodium sources were used, because the type of counter-ion may also influence protein-mineral interactions (Fox, Harper, Holsinger & Pallansch, 1965). The pH of the samples was adjusted to 7.0±0.05 with 1 mol·L$^{-1}$ sodium hydroxide (Sigma-Aldrich GmbH, Steinheim, Germany) or 1 mol·L$^{-1}$ hydrochloric acid (Merck & Co. Inc, Darmstadt, Germany) after stirring for 30 min. Finally, samples were brought to the final protein concentration of 9% w/v with demineralized water. Samples were stored overnight at 20° C. for approximately 17 h. The pH of the samples was adjusted to 7.0±0.05 the next morning, in case deviations had occurred during storage. Deviations that occurred during storage were small and samples did not show any visible spoilage. Samples were analyzed in duplicate for their final pH, calcium-ion activity, turbidity, and viscosity. The samples were also ultracentrifuged, and the pellet and supernatant were collected, weighed and analyzed for their protein content.

Calcium Ion Activity

The calcium ion activity was measured with a Mettler Toledo Seven Multi™ (with an Inlab® Expert Pro pH-meter) calcium measuring device (Mettler Toledo, Greifensee, Switzerland) using an Orion 9300BH electrode and an Orion 900100 reference electrode. Calibration of the electrodes, sample measurements, and calculations of the calcium-ion activities were performed as described in De Kort et al. (2009).

Turbidity

The turbidity was measured with a spectrophotometer (4053 Kinetics, LKB Biochrom, Midland, Canada). Plastic cuvettes with a pathway of 1 cm were used. Measurements were carried out at ambient temperature using a wavelength of 700 nm. Samples were diluted to 10% of their initial dry matter in demineralized water to be within the detection limits of the spectrophotometer.

Viscosity

Samples were analyzed at 20° C. with a MCR 300 rheometer (Anton Paar Physica, Graz, Austria) using a cup (CC27 cylinder) and bob geometry. The viscosity was measured at shear rates of 1 s$^{-1}$ to 1000 s$^{-1}$. Most of the samples behaved close to Newtonian liquids.

Ultracentrifugation

Ultracentrifugation was done with a Centrikon T-1080A ultracentrifuge (Kontron Instruments Ltd., Milano, Italy) with fixed-angle titanium rotor (type TFT 45.94). Samples were ultracentrifuged at 150000 g at 20° C. for 60 minutes. The supernatant and pellet fractions were separated, weighed and analyzed for their protein content.

Protein Content

The protein content was determined in the ultracentrifuged pellets, supernatants and total samples. The NA 2100 Nitrogen and Protein analyzer (CE Instruments, Milan, Italy) was used to determine the nitrogen content in the samples with the Dumas method. A conversion factor of 6.38 was used to convert nitrogen to protein content. Approximately 100 mg of sample was weighed in a tin cup. The sample was dried in an oven at 70° C. for 2.5 hours. Afterwards, 25 mg of absorbens (82009101, Interscience B.V., Breda, The Netherlands) was added and the cup was closed. The cups were placed in the autosampler and analyzed for their nitrogen content.

Voluminosity

The voluminosity of the micelle was calculated in two ways: from viscosity and from ultracentrifugation measurements. The viscosity values were inserted in Eilers' equation (Eilers, 1941) to calculate the volume fraction of the micelles in the solution. The voluminosity of the micelle was calculated from the volume fraction. The viscosity measured at a shear rate of 50 s$^{-1}$ was chosen, as this shear rate corresponds to the organoleptic shear during drinking. A maximum packing volume fraction ($\Phi_{max}$) of 0.79 (Snoeren et al., 1982) was used in the voluminosity calculations. The viscosity of the background electrolyte ($\eta_0$) was set to 1 mPa·s.

The voluminosity of the micelle was also calculated from the ultracentrifugation data by dividing the total pellet volume (mL·g$^{-1}$) by the amount of protein in the pellet (g·g$^{-1}$). The total pellet volume was calculated as described by Van Hooydonk, Hagedoorn & Boerrigter (1986). The volume the minerals occupy in the pellet is negligible, as the proteins dominate the pellet volume. Voluminosity is expressed in mL·g$^{-1}$.

It was verified that the voluminosities of the micelles calculated via viscosity measurements corresponded with the voluminosities of the micelles obtained from ultracentrifugation. The results plotted below are based on viscosity measurements.

LIST OF FIGURES

FIG. 1: Salt equilibria between free calcium ions, calcium chelator complexes, and casein micelles in dairy systems. Chelators in this study are $Na_2UMP$, $Na_2HPO_4$, SHMP, SP, and TSC.

Figure 2:
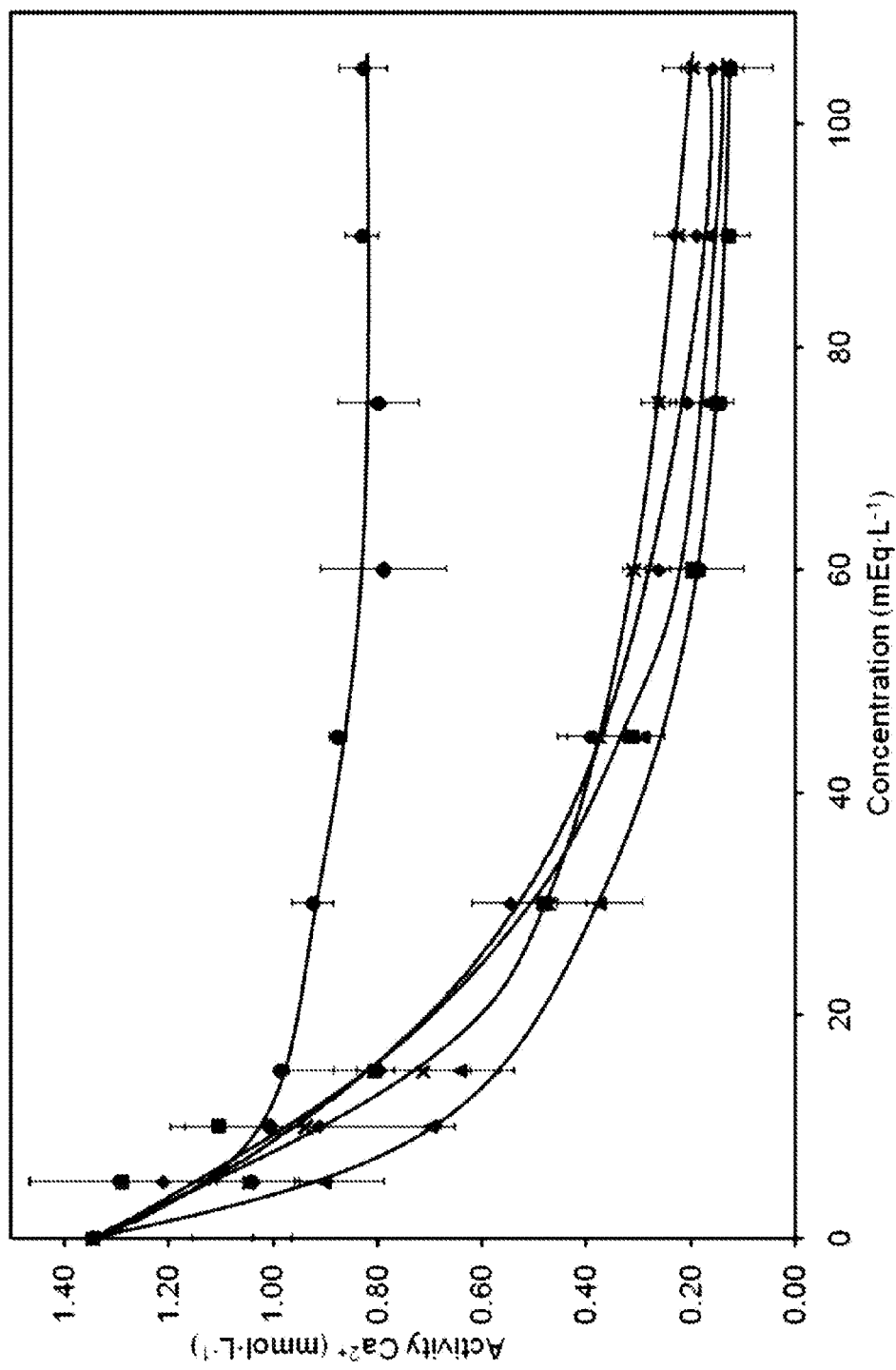

FIG. 2: Calcium ion activity of 9% w/v MCI solution as function of phosphate and citrate concentration. Symbols represent: (●) Na$_2$UMP; (♦) Na$_2$HPO$_4$; (■) SHMP (▲) SP; (x) TSC.

FIG. 3: Viscosity at shear rate 50 s$^{-1}$ of 9% w/v MCI solution as function of phosphate and citrate concentration. Symbols represent: (●) Na$_2$UMP; (♦) Na$_2$HPO$_4$; (■) SHMP (▲) SP; (x) TSC.

Figure 4:
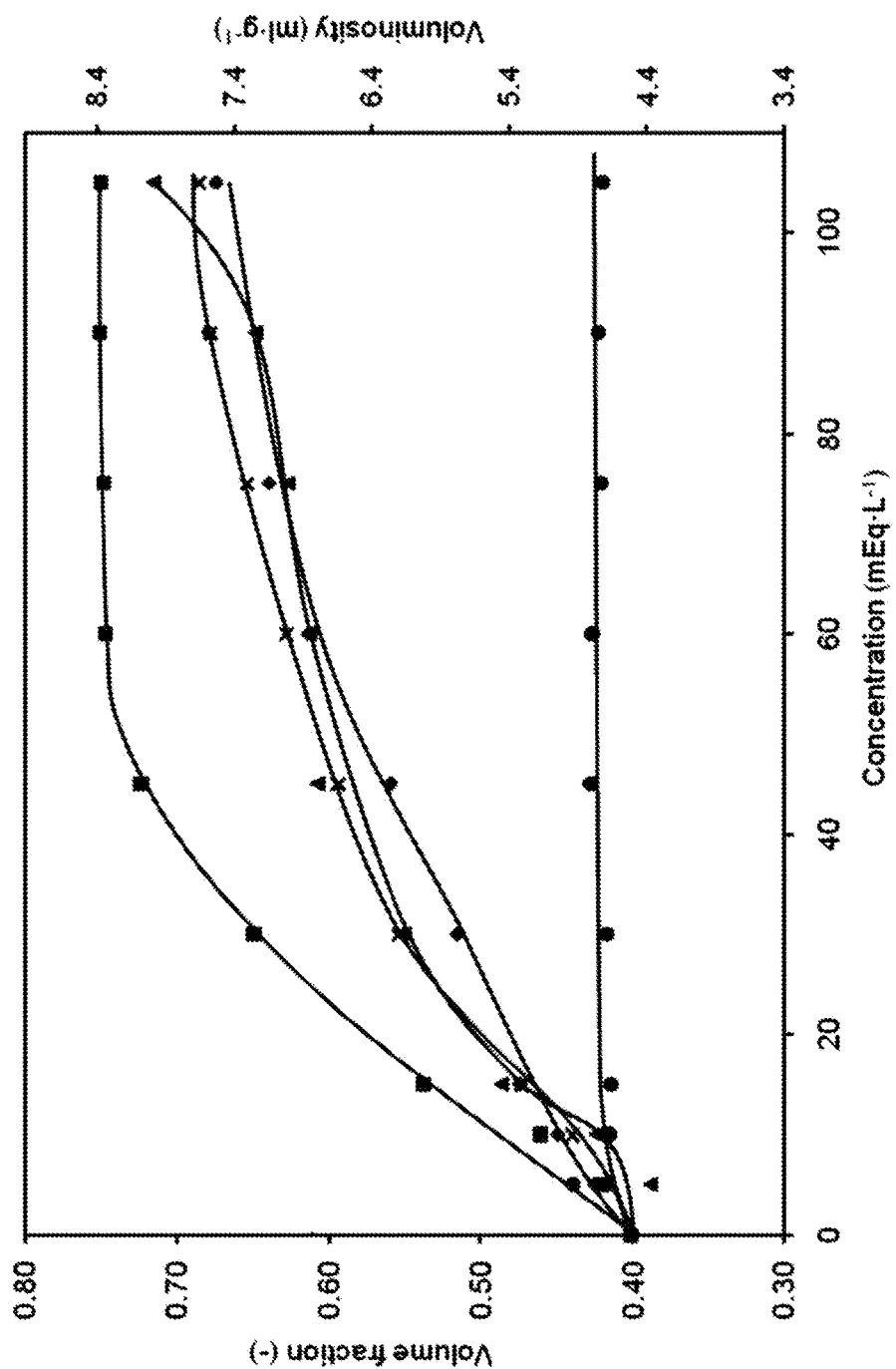

FIG. 4: Voluminosity, calculated with Eilers equation, at shear rate 50 s$^{-1}$ of 9% w/v MCI solution as function of phosphate and citrate concentration. Symbols represent: (●) Na$_2$UMP; (♦) Na$_2$HPO$_4$; (■) SHMP (▲) SP; (x) TSC.

Figure 5:
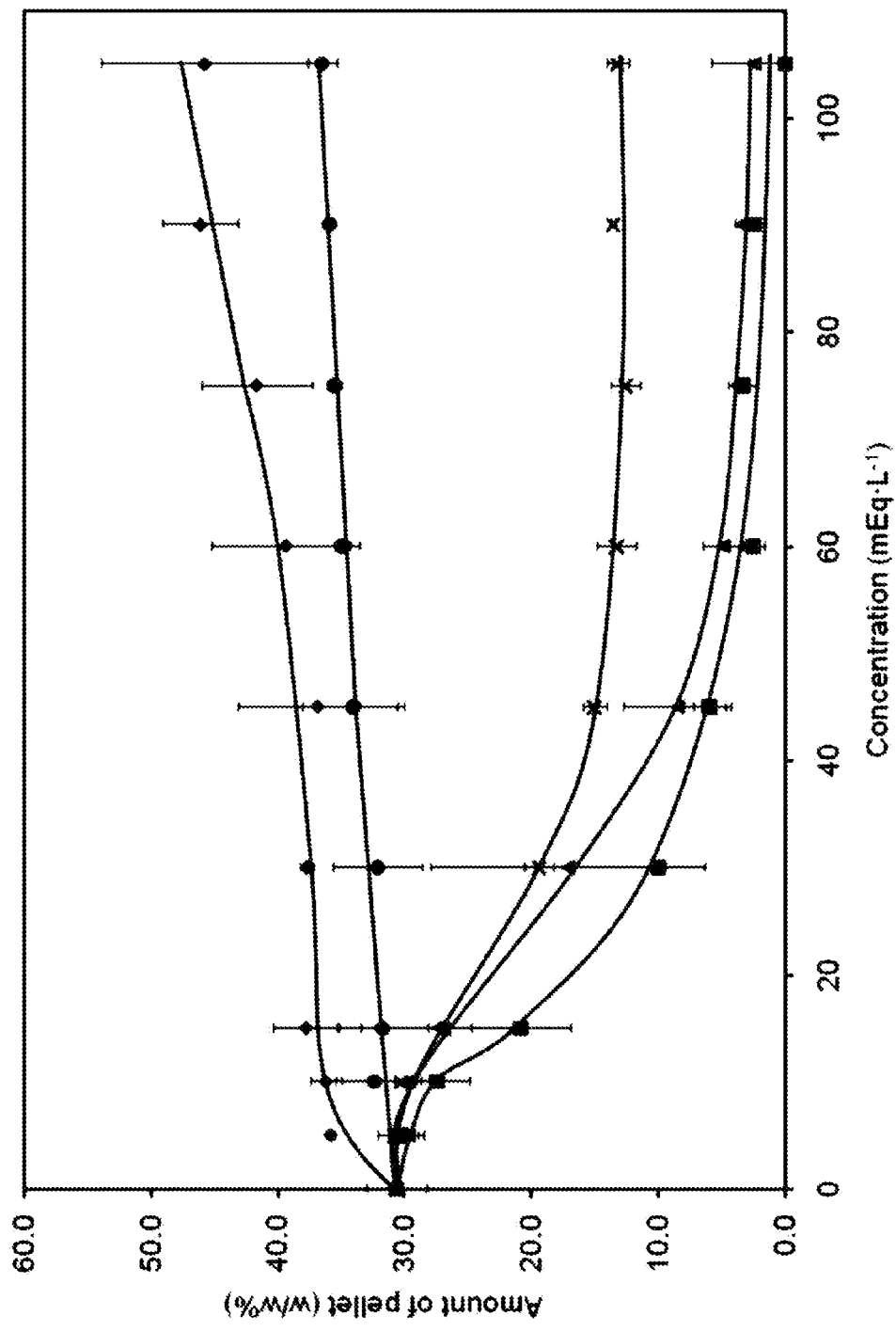

FIG. 5: Amount of ultracentrifuged pellet of 9% w/v MCI solution as function of phosphate and citrate concentration. Symbols represent: (●) Na$_2$UMP; (♦) Na$_2$HPO$_4$; (■) SHMP (▲) SP; (x) TSC.

Figure 6:
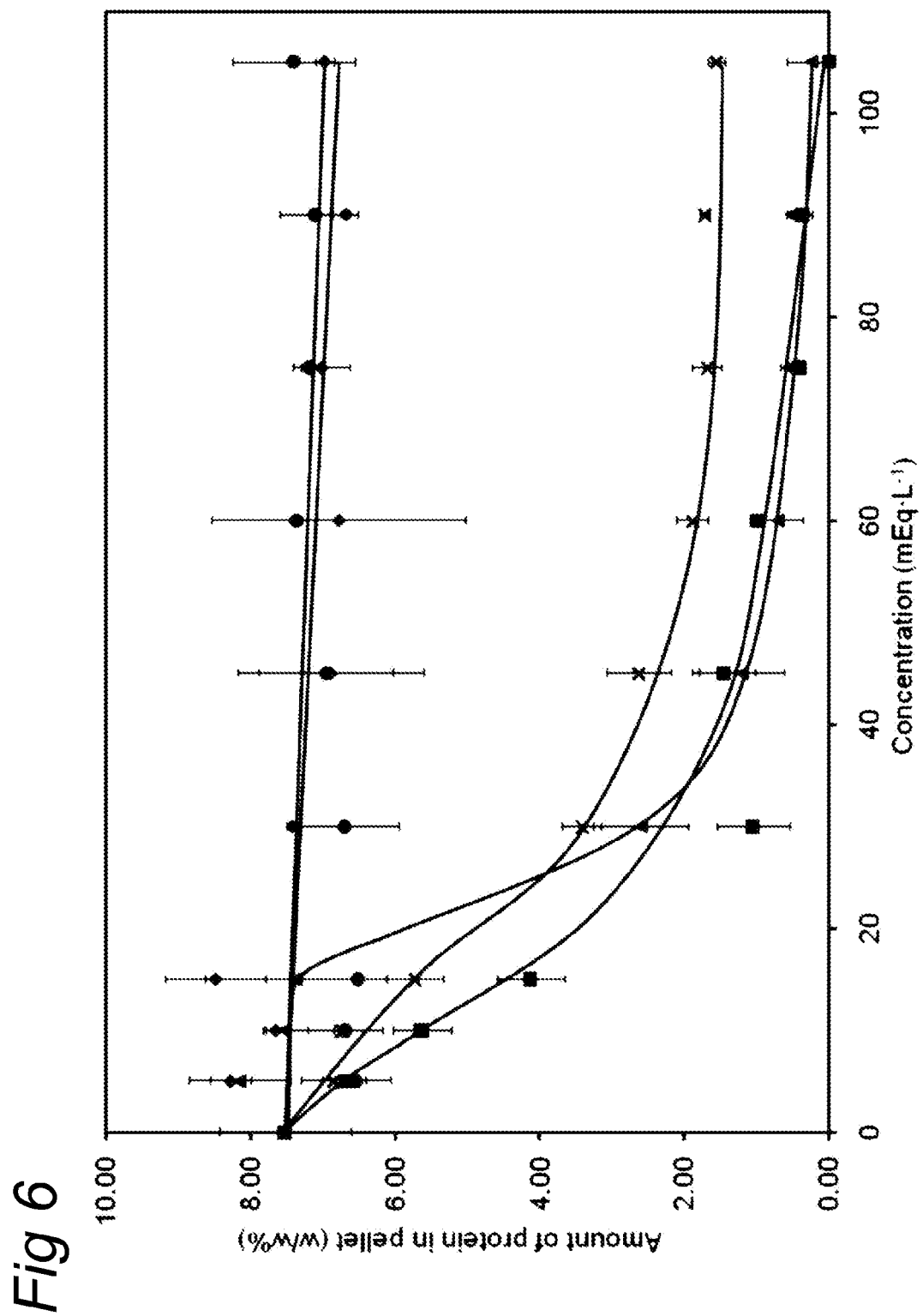

FIG. 6: Amount of protein in ultracentrifuged pellet of 9% w/v MCI solution as function of phosphate and citrate concentration. Symbols represent: (●) Na$_2$UMP; (♦) Na$_2$HPO$_4$; (■) SHMP (▲) SP; (x) TSC.

Figure 7:
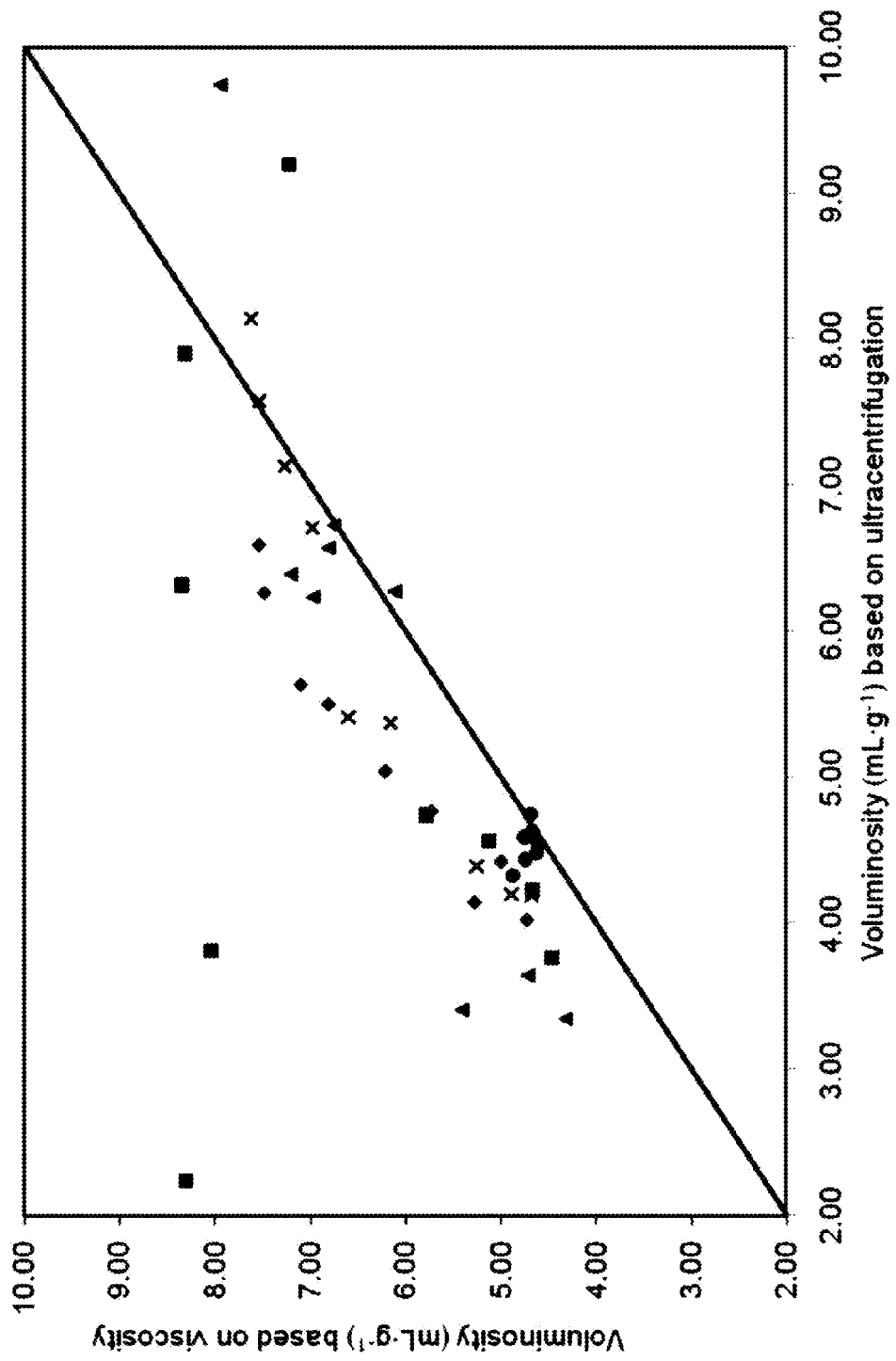

FIG. 7: Correlation between voluminosities based on viscosity and ultracentrifugation measurements. Symbols represent: (D) Na$_2$UMP; (●) Na$_2$HPO$_4$; (■) SHMP (▲) SP; (x) TSC; (-) x=y.

FIG. 8: Turbidity of 9% w/v MCI solution diluted to 10% of their initial dry matter in demineralized water as function of phosphate and citrate concentration. Symbols represent: (●) Na$_2$UMP; (♦) Na$_2$HPO$_4$; (■) SHMP (▲) SP; (x) TSC.

RESULTS AND DISCUSSION

The calcium-ion activity decreases upon addition of the phosphates and citrate (FIG. 2), because calcium ions are chelated from the serum phase and casein micelles. A comparable decrease in calcium-ion activity was measured for SHMP, SP, TSC, and Na$_2$HPO$_4$. The viscosity increased to a comparable extent after addition of SP, TSC, and Na$_2$HPO$_4$ (FIG. 3). The largest increase in viscosity was measured for SHMP samples, which is due to the ability of SHMP to cross-link caseins (Kocak & Zadow, 1985; Mizuno & Lucey, 2007; Vujicic et al., 1968). This resulted in gel formation upon addition of more than 45 mEq·L$^{-1}$ SHMP. The calcium-ion activity only slightly decreased upon addition of Na$_2$UMP, because Na$_2$UMP is a weak calcium binder (De Kort et al., 2009). Accordingly, the viscosity was negligibly affected.

The viscosity values (at a shear rate of 50 s$^{-1}$) were inserted in the formula of Eilers to calculate the voluminosity of the casein micelle. The solutions were shear thinning at higher chelator concentrations (≥75 mEq·L$^{-1}$ for SP, TSC and Na$_2$HPO$_4$ and ≥45 mEq·L$^{-1}$ for SHMP), when higher viscosities were measured. This seems to make interpretation via viscosities at 50 s$^{-1}$ ambiguous. However, in this region of high viscosity, the sensitivity of the volume fraction calculated from Eilers' equation to the actual viscosity value is low: volume fractions are close to the value $\Phi_{max}$ for maximum packing. The results in FIG. 4 show that the casein micelle in a 9% w/v MCI solution has a voluminosity of 4.5 mL·g$^{-1}$. Walstra et al. (2006) measured a voluminosity of 4 mL·g$^{-1}$ for casein micelles in milk. Addition of Na$_2$UMP had a negligible effect on the voluminosity of the casein micelle. Higher volume fractions were calculated for SHMP samples than for the other phosphates and citrate because of gelling of the SHMP samples. For SHMP samples, accordingly, the voluminosity of the casein micelle cannot be deduced from the viscosity via Eilers' equation, because interactions between the micelles are no longer only of hydrodynamic nature. The effect of SP, TSC, and Na$_2$HPO$_4$ on viscosity and thus the derived voluminosity were comparable. The voluminosity of the casein micelle increased from 4.5 mL·g$^{-1}$ ($\Phi$=0.41) to approximately 7.5 mL·g$^{-1}$ ($\Phi$=0.69) upon addition of 105 mEq·L$^{-1}$ SP, TSC, or Na$_2$HPO$_4$. Addition of SP, TSC, and Na$_2$HPO$_4$ neither cross-linked casein micelles nor caused gelation in the studied concentration range, which is in agreement with the behavior of TSC in milk (Mizuno & Lucey, 2005).

The voluminosity of the casein micelle can also be deduced from ultracentrifuged fractions by dividing the total pellet volume by the amount of protein in the pellet. The amount of pellet and amount of protein in the pellet after ultracentrifugation are shown in FIGS. 5 and 6, respectively. The amount of ultracentrifuged pellet is influenced by the time and acceleration of centrifugation, the density and viscosity of the solutions, and the density and size of the casein micelles. The amount of CCP, caseins, and water present in the micelles contributes to the density of the micelles (Lin et al., 1972): the more CCP and caseins are present in (intact) casein micelles and the lower the viscosity, the more easily the micelles precipitate in the pellet. Approximately 30 w/w % pellet was formed with ultracentrifugation for 1 h of 9% w/v MCI and this pellet contained 7.5 w/w % protein. The amount of pellet and the amount of protein in the pellet decreased upon addition of TSC, SP, and SHMP, whereas the amount of pellet increased and the amount of protein in the pellet slightly decreased upon addition of Na$_2$HPO$_4$ and Na$_2$UMP.

FIG. 7 shows the correlation between voluminosities calculated from viscosity and ultracentrifugation measurements. In general, the voluminosities obtained from ultracentrifugation underestimate the voluminosities obtained from viscosity because of compression of the "hairy" outer layer of the micelles in the pellet. This was also observed by Dewan et al. (1972) and Van Hooydonk et al. (1986). The voluminosities correlate for TSC, SP, Na$_2$HPO$_4$, and Na$_2$UMP samples. For SHMP samples, they correlate up to 15 mEq·L$^{-1}$ SHMP, but start to deviate at higher SHMP concentrations. This is due to the high viscosities measured in SHMP samples. The voluminosity of the casein micelle calculated via viscosity measurements is overestimated in SHMP samples, because the caseins were cross-linked. The amount of ultracentrifuged pellet is also lower at higher viscosity. Therefore, the voluminosity of the casein micelle in SHMP samples cannot be calculated either via viscosity or via ultracentrifugation.

Calcium chelators also affect the turbidity of milk solutions (Odagiri & Nickerson, 1964). The turbidity of the 9% w/v micellar casein solution decreased upon addition of the phosphates and citrate in the order SHMP > SP > TSC > Na$_2$HPO$_4$ > Na$_2$UMP (FIG. 8). Mizuno & Lucey (2005) also observed a decrease in turbidity in the order SHMP > TSC > Na$_2$HPO$_4$ in samples prepared from milk protein concentrate at pH 5.8. The turbidity decreased to a comparable extent after addition of 45 mEq·L$^{-1}$ SP or SHMP, whereas large differences in viscosity were measured for these samples. This implies that SHMP has the ability to cross-link caseins in this concentration range, whereas SP does not. Our hypothesis is that this is due to the form and charge distribution around the molecules. SHMP has six homogeneously distributed negative charges around its molecule, whereas SP has twelve negative charges, clustered in pairs, around its molecule. This homogeneous charge distribution enables SHMP to interact with cations and the caseins at the same time. SP can approach the caseins less easily than SHMP because of the charge distribution around the SP molecule and, in this way, cross-linking is inhibited. SP also is a very strong calcium chelator and might immediately chelate free calcium ions to such an extent that no charges or calcium ions are any longer available for cross-linking the caseins. This was measured as a stronger decrease in calcium-ion activity for SP than SHMP (FIG. 2). Mizuno and Lucey (2007) investigated the cross-linking ability of tetrasodium pyrophosphate (TSPP) in milk protein concentrate solution. They suggested that calcium pyrophosphate complexes cross-link caseins or reduce electrostatic repulsion between caseins, which facilitates hydrophobic association. TSPP probably cross-links the caseins more easily than SHMP, as it has only four homogeneously distributed charges around its molecule. Nevertheless, further research is required to elucidate the exact mechanism of cross-linking caseins by different polyphosphates.

It is remarkable that SP, TSC, and $Na_2HPO_4$ demonstrate a comparable increase in viscosity and voluminosity and decrease in calcium-ion activity, while these chelators have a different impact on turbidity and ultracentrifuged (protein in) pellet. Calcium ions in the casein micelle are bound to the phosphoserine residues or are part of the CCP complexes. The added chelator competes with the phosphoserine residues and CCP in the casein micelle for the calcium ions. Due to the differences in affinity for calcium ions of SP, TSC, and $Na_2HPO_4$ (De Kort et al., 2009; Mekmene, Le Graet & Gaucheron, 2009; Turner, Paphazy, Haygarth & Mckelvie, 2002; Upreti, Buhlmann & Metzger, 2006), the chelators are able to release different amounts of CCP from the micelle. This does not necessarily affect the integrity of the micellar structure, because hydrophobic interactions between caseins that surround the CCP clusters prevent the micelles from complete dissociation when CCP is solubilized (Mcmahon & Oommen, 2007; Munyua & Lars son-Raznikiewicz, 1980).

In general, scattering of particles is determined by the concentration, particle size, and refractive index relative to that of the solution (Van De Hulst, 1957). The caseins and CCP are mainly responsible for the light scattering properties of the casein micelle (Munyua & Larsson-Raznikiewicz, 1980). Removal of CCP from the micelles reduces the refractive index of the casein micelles, which is measured as a decrease in turbidity of the milk solutions. The study of Smiddy, Martin, Kelly, & De Kruif (2006) on internally cross-linked casein micelles showed that after addition of 50 $mmol \cdot L^{-1}$ citrate (150 $mEq \cdot L^{-1}$) to skim milk a decrease in light scattering of approximately 50% was measured. These authors suggested that all CCP (7% of dry mass of the casein micelle) was removed from the cross-linked micelles at this concentration, while the micellar structure remained intact. We measured a decrease in turbidity of 97% for SHMP and SP, 87% for TSC, and 60% for $Na_2HPO_4$ upon addition of 105 $mEq \cdot L^{-1}$ chelator to 9 w/v % MCI solution (FIG. 8). Hence, these decreases in turbidity cannot only be attributed to release of CCP from the micelle. Some specific casein may also be released from the casein micelle upon removal of calcium and CCP from the micelle. Only a slight decrease in the amount of protein in the pellet was measured for $Na_2HPO_4$ samples (FIG. 6), whereas a much larger decrease in amount of protein in the pellet was measured for SP and TSC samples. However, the viscosity of $Na_2HPO_4$ samples increased to comparable extents as the viscosity of TSC and SP samples. This illustrates that the difference in decrease in turbidity for SP, TSC, and $Na_2HPO_4$ samples cannot be explained by the release of only CCP and some specific caseins from the micelles. Hence, the change in refractive index and concentration of particles is not sufficient to cause the strong decrease in turbidity. Rayleigh scattering indicates that the intensity of the scattered light varies as the sixth power of the particle size (Van De Hulst, 1957) and accordingly particle size makes the main contribution to the change in turbidity of the solution. The particle size of the casein micelles is affected, when the micelles swell or dissociate into smaller structures. Huppertz (2007) described that addition of 6 $mol \cdot^{-1}$ urea to internally cross-linked casein micelles induces swelling of the micelles, which is measured as a decrease in turbidity of 40%. The decrease in turbidity in our MCI samples is too large to be only attributed to the swelling of the casein micelles. A further explanation on the swelling of the casein micelles will be described hereafter. The major decrease in turbidity is most likely due to the dissociation of the casein micelles into smaller structures. Dissociated micelles will precipitate less easily than intact casein micelles during ultracentrifugation, because the fragments of the dissociated micelles are smaller and lighter than the intact casein micelles. Based on these phenomena, the turbidity and ultracentrifugation results indicate that micellar dissociation occurred to the largest extent for addition of SHMP and SP, followed by TSC and finally by $Na_2HPO_4$. Micellar dissociation most probably did not occur in $Na_2UMP$ samples.

Nevertheless, a comparable voluminosity can be deduced for the addition of SP, TSC, or $Na_2HPO_4$ in solutions containing dissociated or intact casein micelles, because the total volume per gram of protein is unchanged. This indicates that e.g. the voluminosity of the intact micelle in a $Na_2HPO_4$ solution is comparable to the voluminosity of the dissociated micelle in a SP solution as long as the calcium-ion activities are comparable in both solutions. As a result, a comparable increase in viscosity and voluminosity of the casein micelle was measured for SP, TSC, and $Na_2HPO_4$ samples. The phenomenon of milk solutions containing intact and dissociated casein micelles upon addition of polyphosphate or EDTA was introduced previously by e.g. Lin et al. (1972), Griffin et al. (1988), Panouillé et al. (2005) and Pitkowski et al. (2009).

As mentioned, the casein micelles will also swell upon addition of calcium chelators. FIG. 2 shows that the calcium-ion activity decreased to a comparable extent upon addition of SHMP, SP, TSC, and $Na_2HPO_4$. The electrostatic repulsion in the casein micelles increased because of the decrease in free calcium ions in the continuous phase. Consequently, the casein micelles became more hydrated and swelled, which is measured as an increase in viscosity of the MCI solutions (FIG. 3) and also an increase in voluminosity of the casein micelle (FIGS. 4 and 7). The phenomenon of swelling of the casein micelles can be derived from the ultracentrifuged pellet in $Na_2HPO_4$ samples (FIG. 5). In these samples the pellet volume increased at higher chelator concentrations, whereas in SHMP, SP, or TSC samples the pellet volume decreased. The density, molecular weight, and size of the casein micelles are important for the amount of ultracentrifuged pellet obtained and are determined by the amount of casein, CCP, and water present in the casein micelles (Walstra et al., 2006). Gaucher et al. (2007) and Guo et al. (2003) observed that orthophosphate precipitates with calcium in the casein micelles. For example, an amount of approximately 3 g $Ca_3(PO_4)_2$ can be formed upon addition of 60 $mEq \cdot L^{-1}$ $Na_2HPO_4$, of which a large part of the calcium ions are already part of the casein micelles. The increase in molecular weight is negligible in comparison to the observed increase in amount of pellet. This increase is ascribed to the swelling of the caseins. FIG.

5 also shows that the casein micelle slightly swells upon addition of Na$_2$UMP, because the amount of pellet increased in these samples as well. These findings of swelling of the micelles upon addition of EDTA were not observed by Lin et al. (1972) and Pitkowski et al. (2009). They both described that at certain EDTA concentrations only a fraction of the micelles dissociated, but that the hydrodynamic radius of the residual casein micelles remained constant. However, Sood & Gaind (1979) already questioned the observations of Lin et al. (1972) that intact micelles will remain at a constant radius, because they measured an increase in voluminosity upon addition of EDTA. Therefore, they concluded that the micelles should be able to swell or shrink when the calcium content in the casein micelles is changed. Moreover, Huppertz et al. (2007) showed by three light scattering methods that even internally cross-linked casein micelles were able to swell upon addition of citrate or urea, which was measured as an increase in particle sizes and decrease in turbidity. These results are in line with our observations that addition of calcium chelators will induce swelling of the intact casein micelles and dissociation of a fraction of the micelles. This also suggests that loosely bound calcium, i.e. bound to the negatively charged amino acids side chains and phosphate groups, is present in the casein micelle besides strongly bound calcium in the CCP complexes. The former type has a structural function and its release is related to swelling of the micelle, which is measured as an increase in viscosity. Release of the latter is related to the dissociation of the casein micelles, which is measured as a decrease in turbidity and amount of ultracentrifuged pellet. The hypothesis that two types of calcium interactions are present in the casein micelle was proposed by Munyua & Larsson-Raznikiewicz (1980). Overall, it seems that the calcium-ion activity is a good predictor for the observed viscosities and voluminosities, but a poor indicator when the casein micelle starts to dissociate.

CONCLUSION

Calcium chelators induce physical changes in concentrated micellar casein solutions by affecting the microstructure of the casein micelles. Addition of Na$_2$HPO$_4$, TSC, and SP caused a comparable increase in viscosity of the MCI solutions, whereas the turbidity decreased in the order SP> TSC > Na$_2$HPO$_4$. Addition of SP or SHMP gave a comparable decrease in turbidity, but the viscosity of SHMP samples was much higher. This is due to the ability of SHMP to cross-link casein micelles. The calcium-ion activity decreased to a comparable extent upon addition of SHMP, SP, TSC, or Na$_2$HPO$_4$, which induced swelling of the casein micelles.

The voluminosity of the casein micelle (i.e. swelling) could be calculated from the viscosity and ultracentrifugation measurements for addition of SP, TSC, Na$_2$HPO$_4$, and Na$_2$UMP. The voluminosities obtained from the two calculation methods correlate for these samples. The voluminosity of the casein micelle in SHMP samples could not be derived from viscosity and ultracentrifugation results because of the cross-links formed between the caseins. The weak calcium chelator Na$_2$UMP had a negligible effect on the viscosity and turbidity of the MCI solution and only slightly decreased the calcium-ion activity. The decrease in calcium-ion activity was predictive for the increase in viscosity and related swelling of the micelle until the micelle starts to dissociate. This confirms the hypothesis that two types of calcium interactions are present in the casein micelle. The extent of micellar dissociation is dependent on the type and concentration of added calcium chelator.

REFERENCES de Kort, E. J. P., M. Minor, T. H. M. Snoeren, A. C. M. van Hooijdonk, and E. van der Linden. 2009. Calcium binding capacity of organic and inorganic ortho- and polyphosphates. Journal of dairy science and technology. 89:283-299.

Dewan, R. K., V. A. Bloomfield, A. chudgar, and C. V. Morr. 1972. Viscosity and voluminosity of bovine milk casein micelles. J. Dairy Sci. 56(6):699-705.

Eilers, H. (1941). Die Viskositat von emulsionen hochviskoser stoffe als funktion der konzentration. Kolloid Zeitschrift. Zeitschrift fur wissenschaftliche und technische kolloidchemie, 96, 313-321.

Eilers, H. 1945. Colloidchemische studien aan ondermelk. Vol. 50, 15. Koninklijke Nederlandse Zuivelbond, 's-Gravenhage.

Fox, K. K., M. K. Harper, V. H. Holsinger, and M. J. Pallansch. 1965. Gelation of milk solids by orthophosphate. J. Dairy Sci. 48:179-185.

Gaucher, I., Piot, M., Beaucher, E., & Gaucheron, F. (2007). Physico-chemical characterization of phosphate-added skim milk. *International Dairy Journal*, 17, 1375-1383.

Griffin, M. C. A., Lyster, R. L. J., & Price, J. C. (1988). The disaggregation of calcium-depleted casein micelles. *European Journal of Biochemistry*, 174, 339-343.

Griffin, M. C. A., Price, J. C., & Griffins, W. G. (1989). Variation of the viscosity of a concentrated, sterically stabilized, colloid: effect of ethanol on casein micelles of bovine milk. *Journal of colloid and interface science*, 128 (1), 223-229.

Guo, C., B. E. Campbell, K. Chen, A. M. Lenhoff, and O. D. Velev. 2003. Casein precipitation equilibria in the presence of calcium ions and phosphates. Colloids and Surfaces B: Biointerfaces. 29:297-307.

Hallstrom, M. and P. Dejmek. 1988. Rheological properties of ultrafiltered skim milk. II. Protein voluminosity. Milchwissenschaft. 43(2):95-97.

Harwalkar, V. R. 1982. Chapter 7: Age gelation of sterilised milks. Pages 229-269 in Developments in dairy chemistry. Vol. 1. P. F. Fox, ed. Applied Science Publishers, London.

Huppertz, T., Smiddy, M. A., & De Kruif, C. G. (2007). Biocompatible micro-gel particles from cross-linked casein micelles. *Biomacromolecules*, 8, 1300-1305.

Holt, C. 1997. The milk salts and their interaction with casein. Advanced Dairy Chemistry. 3:233-256.Karlsson, A. O., R. Ipsen, K. Schrader, and Y. Ardo. 2005. Relationship between physical properties of casein micelles and rheology of skim milk concentrate. J. Dairy Sci. 88:3784-3797.

Kocak, H. R. and J. G. Zadow. 1985. Controlling age gelation of UHT milk with additives. The australian journal of dairy technology. 40:58-64.

Korolczuk, J. (1981). Voluminosity and viscosity of casein solution I. The correlation between the voluminosity, protein concentration and viscosity. *Milchwissenschaft*, 36 (7), 414-416.

Krieger, I. M. (1972). Rheology of monodisperse latices. *Advances in colloid and interface science*, 3, 111-136.

Leviton, A. and M. J. Pallansch. 1962. High-temperature-short time-sterilised evaporated milk. IV. The retardation of gelation with condensed phosphates, manganous ions, polyhydric compounds, and phosphatides. *J. Dairy Sci.* 45:1045-1056.

Lin, S. H. C., Leong, S. L., Dewan, R. K., Bloomfield, V. A., & Morr, C. V. (1972). Effect of calcium ion on the structure of native bovine casein micelles. *Biochemistry,* 11 (10), 1818-1821.

Marchin, S., Puteaux, J.-L., Pignon, F., & Léonil, J. (2007). Effects of the environmental factors on the casein micelle structure studied by cryo transmission electron microscopy and small-angle x-ray scattering/ultrasmall-angle x-ray scattering. *The journal of chemical physics,* 126 (045101).

McMahon, D. J., & Oommen, B. S. (2007). Supramolecular structure of the casein micelle. *Journal of Dairy Science,* 91, 1709-1721.

Mekmene, O., Le Graet, Y., & Gaucheron, F. (2009). A model for predicting salt equilibria in milk and mineral-enriched milks. *Food Chemistry,* 116, 233-239.

Mizuno, R. and J. A. Lucey. 2005. Effects of emulsifying salts on the turbidity and calcium-phosphate-protein interactions in casein micelles. *J. Dairy Sci.* 88:3070-3078.

Mizuno, R. and J. A. Lucey. 2007. Properties of milk protein gels formed by phosphates. *J. Dairy Sci.* 90:4524-4531.

Morr, C. V. 1967. Some effects of pyrophosphate and citrate ions upon the colloidal caseinate-phosphate micelles and ultrafiltrate of raw and heated skimmilk. *J. Dairy Sci.* 50:1038-1044.

Munyua, J. K., & Larsson-Raznikiewicz, M. (1980). The influence of $Ca^{2+}$ on the size and light scattering properties of casein micelles 1. $Ca^{2+}$ removal. *Milchwissenschaft,* 35 (10), 604-606.

Odagiri, S., & Nickerson, T. A. (1964). Complexing of calcium by hexametaphosphate, oxalate, citrate, and EDTA in milk. I. Effects of complexing agents of turbidity and rennet coagulation. *Journal of Dairy Science,* 47, 1306-1309.

Panouillé, M., Nicolai, T., Benyahia, L., & Durand, D. (2005). Aggregation and gelation of casein sub-micelles. *Special publication—Royal society of chemistry,* 298, 194-208.

Philippe, M., F. Gaucheron, Y. Le Graet, F. Michel, and A. Garem. 2003. Physicochemical characterisation of calcium-supplemented skim milk. *Lait.* 83:45-59.

Pitkowski, A., Nicolai, T., & Durand, D. (2009). Scattering and turbidity study of the dissociation of casein by calcium chelation. *Biomacromolecules,* 9, 369-375.

Smiddy, M. A., Martin, J.-E. G. H., Kelly, A. L., De Kruif, C. G., & Huppertz, T. (2006). Stability of casein micelles cross-linked by transglutaminase. *Journal of Dairy Science,* 89, 1906-1914.

Snoeren, T. H. M., Damman, A. J., & Klok, H. J. (1982). The viscosity of skim-milk concentrates. *Netherlands milk and dairy journal,* 36, 305-316.

Sood, S. M., & Gaind, D. K. (1979). Correlation between micelle solvation and calcium content. *New Zealand Journal of Dairy Science and Technology,* 14, 32-34.

Turner, B. L., M. J. Paphazy, P. M. Haygarth, and I. D. McKelvie. 2002. Inositol phosphates in the environment. *Philosophical Transactions of the Royal Society of London. Series B, Biological Sciences.* 357:449-469.

Udabage, P., McKinnon, I. R., & Augustin, M.-A. (2000). Mineral and casein equilibria in milk: effects of added salts and calcium-chelating agents. *Journal of Dairy Research,* 67, 361-370.

Upreti, P., P. Buhlmann, and L. E. Metzger. 2006. Influence of calcium and phosphorus, lactose and salt-to moisture ratio on cheddar cheese quality: pH buffering properties of cheese. *J. Dairy Sci.* 89:938-950.

Van de Hulst, H. C. (1957). *Light scattering in small particles.* New York, USA: Wiley.

van Hooydonk, A. C. M., Hagedoorn, H. G., & Boerrigter, I. J. (1986). pH-induced physico-chemical changes of casein micelles in milk and their effect on renneting. 1. Effect of acidification on physico-chemical properties. *Netherlands milk and dairy journal,* 40, 281-296.

Vujicic, I., J. M. deMan, and I. L. Woodrow. 1968. Interaction of polyphosphates and citrate with skimmilk proteins. *Canadian Institute of Food Science and Technology Journal.* 1:17-21.

Walstra, P., J. T. M. Wouters, and T. J. Geurts. 2006. *Dairy science and technology.* 2 ed. CRC press, Boc Raton, USA.

Ward, B. R., Goddard, S. J., Augustin, M.-A., & McKinnon, I. R. (1997). EDTA-induced dissociation of casein micelles and its effect on foaming properties of milk. *Journal of Dairy Research,* 64, 495-504.

Zittle, C. A. 1966. Precipitation of casein from acidic solutions by divalent anions. *J. Dairy Sci.* 49:361-364.

The invention claimed is:

1. A liquid nutritional composition comprising:
    (a) 9 to 20 g of protein per 100 ml of the composition and having a pH of about 6 to 8, in which 70-100% of said protein comprises micellar casein, and
    (b) about 20 to 120 $mEq.L^{-1}$ of one or more chelating agents selected from the group consisting of a phosphoric acid, citric acid, cytidine monophosphate, orthophosphate, inositol hexaphosphate, hexametaphosphate, a soluble citrate salt, and mixtures thereof.

2. The liquid nutritional composition according to claim 1, wherein the one or more chelating agents are selected from the group consisting of orthophosphate, inositol hexaphosphate, hexametaphosphate, and a mixture thereof.

3. The liquid nutritional composition according to claim 1, wherein the one or more chelating agents are selected from the group consisting of disodium cytidine monophosphate, disodium orthophosphate, dodecasodium inositol hexaphosphate, hexasodium hexametaphosphate, trisodium citrate, and mixtures thereof.

4. The liquid nutritional composition according to claim 1, wherein the chelating agent is selected from the group consisting of a phosphoric acid, citric acid, orthophosphate, inositol hexaphosphate, hexametaphosphate, a soluble citrate salt, and mixtures thereof.

5. The liquid nutritional composition according to claim 1, further comprising one or more of fat, digestible carbohydrates and non-digestible carbohydrates.

6. A nutritional composition comprising:
    (a) 9 to 20 g of protein per 100 ml of the composition and having a pH of about 6 to 8, in which 70-100% of said protein comprises micellar casein, and
    (b) 20 to 120 $mEq.L^{-1}$ of one or more chelating agents selected from the group consisting of cytidine monophosphate, orthophosphate, inositol hexaphosphate, hexametaphosphate, citrate, and a mixture thereof,
    wherein citric acid, a soluble citrate salt or a mixture thereof is excluded as the sole chelating agent.

7. The nutritional composition according to claim 6, wherein the one or more chelating agents are selected from the group consisting of disodium cytidine monophosphate, disodium orthophosphate, dodecasodium inositol hexaphosphate, hexasodium hexametaphosphate, trisodium citrate, and a mixture thereof.

8. The nutritional composition according to according to claim 6, comprising about 20 to 100 mEq.L$^{-1}$ of the one or more chelating agents.

9. The nutritional composition according to claim 6, comprising one or more of fat, digestible and non-digestible carbohydrates.

10. The nutritional composition according to claim 6, wherein the composition is a liquid composition.

11. A method of providing nutrition to a person in need thereof, comprising administering to the person a liquid nutritional composition comprising:
   (a) 9 to 20 g of protein per 100 ml of the composition and having a pH of about 6 to 8, in which 70-100% of said protein comprises micellar casein, and
   (b) about 20 to 120mEq.L$^{-1}$ of one or more chelating agents selected from the group consisting of a phosphoric acid, citric acid, cytidine monophosphate, orthophosphate, inositol hexaphosphate, hexametaphosphate, a soluble citrate salt, and mixtures thereof.

12. The method according to claim 11, wherein the person is an elderly person, a person that is in a disease state, a person that is recovering from a disease state, a person that is malnourished, or a healthy person such as a sportsman or sportswoman or an active elderly.

13. A method of providing nutrition to a person in need thereof, comprising administering to the person a nutritional composition according to claim 6.

14. The method according to claim 13, wherein the person is an elderly person, a person that is in a disease state, a person that is recovering from a disease state, a person that is malnourished, or a healthy person such as a sportsman or sportswoman or an active elderly.

\* \* \* \* \*